(12) United States Patent
Usuda

(10) Patent No.: US 12,300,386 B2
(45) Date of Patent: May 13, 2025

(54) INFORMATION PROCESSING APPARATUS, TRAINING DATA GENERATION DEVICE, AND DIAGNOSIS SUPPORT SYSTEM

(71) Applicant: FUJIFILM Corporation, Tokyo (JP)

(72) Inventor: Toshihiro Usuda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 282 days.

(21) Appl. No.: 17/930,770

(22) Filed: Sep. 9, 2022

(65) Prior Publication Data
US 2023/0082499 A1     Mar. 16, 2023

(30) Foreign Application Priority Data

Sep. 10, 2021   (JP) ................................. 2021-148161

(51) Int. Cl.
*G16H 50/20*       (2018.01)
*G06T 7/00*        (2017.01)
(Continued)

(52) U.S. Cl.
CPC .......... *G16H 50/20* (2018.01); *G06T 7/0012* (2013.01); *G06T 7/11* (2017.01); *G06V 10/774* (2022.01); *G06T 2207/20104* (2013.01)

(58) Field of Classification Search
CPC ........ G16H 50/20; G16H 30/40; G16H 50/70; G06T 7/0012; G06T 7/11; G06T 2207/20104; G06T 2207/20081; G06T 2207/20084; G06T 2207/30004; G06V 10/774; G06V 2201/03
(Continued)

(56) References Cited

U.S. PATENT DOCUMENTS

2005/0010445 A1   1/2005  Krishnan et al.
2016/0171299 A1*  6/2016  Lee ..................... G06F 3/04842
                                                          382/128
(Continued)

FOREIGN PATENT DOCUMENTS

JP   2007-528746 A   10/2007
JP   2018-120300 A    8/2018
(Continued)

OTHER PUBLICATIONS

Shimabaram Y et al.; "Efficient development of medical image diagnosis support systems using artificial intelligence"; Jul. 25, 2017; total 8 pages; 15(9); Rad Fan, Medical Eye Co., Ltd.
(Continued)

*Primary Examiner* — Jacky X Zheng
(74) *Attorney, Agent, or Firm* — Studebaker Brackett PLLC

(57) ABSTRACT

An information processing apparatus detects, by a first detector, a region-of-interest reflected in medical image data, performs a control of displaying, on a display, the medical image data which is a detection result indicating that the region-of-interest is not detected, receives information for specifying the medical image data evaluated that the detection result is false negative by a user, re-detects, by a second detector, the region-of-interest based on the false negative medical image data, and trains the first detector using a first medical image data set including the medical image data and a re-detection result.

20 Claims, 19 Drawing Sheets

(51) Int. Cl.
*G06T 7/11* (2017.01)
*G06V 10/774* (2022.01)

(58) Field of Classification Search
USPC .......................................................... 382/128
See application file for complete search history.

(56) References Cited

U.S. PATENT DOCUMENTS

| 2018/0211374 | A1  | 7/2018  | Tanaka et al. |            |
|--------------|-----|---------|---------------|------------|
| 2020/0342267 | A1  | 10/2020 | Usuda         |            |
| 2020/0402663 | A1* | 12/2020 | Nagai         | G16H 50/20 |
| 2021/0366110 | A1* | 11/2021 | Oosake        | G06T 7/0012 |

FOREIGN PATENT DOCUMENTS

| JP | 2020-154798 A  | 9/2020 |
| KR | 2016-0071242 A | 6/2016 |
| WO | 2019/150813 A1 | 8/2019 |

OTHER PUBLICATIONS

Shin, Y et al.; "Automation Colon Polyp Detection Using Region Based Deep CNN and Post Learning Approaches"; Jul. 20, 2018; pp. 40950-40962; vol. 6; IEEE [Retrieved Mar. 21, 2025]; Internet: URL: http://ieeexplore.org/stamp.stamp.jsp?tp=arnumber=8416731 &tag=1>; DOI: 10.1109/ ACCESS.2018.2856402.

"Notice of Reasons for Refusal" Office Action issued in JP 2021-148161; mailed by the Japanese Patent Office on Apr. 1, 2025.

\* cited by examiner

INFORMATION PROCESSING APPARATUS, TRAINING DATA GENERATION DEVICE, AND DIAGNOSIS SUPPORT SYSTEM

CROSS-REFERENCE TO RELATED APPLICATIONS

This application claims priority under 35 U.S.C. § 119(a) to Japanese Patent Application No. 2021-148161 filed on 10 Sep. 2021. The above application is hereby expressly incorporated by reference, in its entirety, into the present application.

BACKGROUND OF THE INVENTION

1. Field of the Invention

The present invention relates to an information processing apparatus, a training data generation device, and a diagnosis support system.

2. Description of the Related Art

In the medical field, information for supporting a diagnosis of a doctor is obtained by performing image recognition processing using a medical image obtained by various modalities, such as an endoscope, a computed tomography (CT), or magnetic resonance imaging (MRI). In recent years, various methods of obtaining desired information by the image recognition processing using a machine learning technique have been developed.

Various ideas for performing the image recognition processing using the machine learning technique have been studied. For example, in a defect determination method of a manufactured product, a method is known in which the presence or absence of an abnormal region is appropriately determined using a first model for discriminating a high-quality image, and a second model generated for discriminating between correct answer data and non-correct answer data using correct answer data and non-correct answer data for discriminating an abnormality candidate region by a user, so that sufficient examination accuracy can be obtained by suppressing erroneous detection of a non-defect portion of a detection target (JP2018-120300A, corresponding to US2018/211374A1).

In addition, there is known an image examination device that, in order to shorten an expected value of a time required for a determination by image recognition processing, determines a state of an object using a first neural network and determines the state of the object using a second neural network in a case in which the state of the object does not satisfy a predetermined condition (JP2020-154798A).

In addition, there is known a data processing device that, in order to improve the recognition accuracy for rare case data, corrects, by a user, a result of the recognition recognized by a recognition unit that performs image recognition processing, performs weighting on the corrected data, uses the weighted data as training data, and performs learning of the recognition unit including the training data (WO2019/150813A, corresponding to US 2020/342267A1).

SUMMARY OF THE INVENTION

In a case in which image recognition processing using machine learning technique is performed, in a case in which a learning model constructed by supervised learning is used, it is preferable to use a learning model constructed by being trained using a large number of high-quality training data. It should be noted that an appropriate annotation is required for the training data in this case.

Therefore, in a case in which the image recognition processing of the medical image is performed with high accuracy, it is preferable to use a learning model that has been trained using many types and a large number of medical images to with an appropriate annotation is added, as the training data. In addition, in a case in which the accuracy of the image recognition processing is improved in the already constructed learning model, it is preferable to prepare effective training data and an annotation for improving the accuracy and to perform learning using the training data.

However, it takes a lot of effort to collect many types and a large number of medical images that are effective for improving the accuracy of the learning model, and to add an appropriate annotation to the medical images.

The present invention is to provide an information processing apparatus, a training data generation device, and a diagnosis support system capable of efficiently improving the detection accuracy in a case in which a region-of-interest is detected using a medical image.

An aspect of the present invention relates to an information processing apparatus comprising a processor, in which the processor acquires medical image data in which an examination target is reflected, detects, by a first detector, a region-of-interest including the examination target reflected in the medical image data based on the medical image data, performs a control of displaying, on a display, the medical image data which is a detection result indicating that the region-of-interest is not detected, receives information for specifying the medical image data evaluated that the detection result is false negative by a user, re-detects, by a second detector, the region-of-interest including the examination target reflected in the medical image data based on the medical image data evaluated as false negative, generates a first medical image data set including the medical image data and a re-detection result of the region-of-interest of the medical image data, and trains the first detector using the first medical image data set.

It is preferable that an operation load of the second detector be higher than an operation load of the first detector.

It is preferable that the second detector be constructed using a machine learning algorithm, and the number of parameters of the second detector be larger than the number of parameters of the first detector.

It is preferable that the second detector re-detect the region-of-interest based on the medical image data having a high resolution as compared with the first detector.

It is preferable that the second detector re-detect the region-of-interest based on each of a plurality of the medical image data, and the processor integrate a plurality of the re-detection results based on the plurality of medical image data, respectively, into the re-detection result by the second detector.

It is preferable that a plurality of the second detectors be present, and each of the second detectors re-detect the region-of-interest based on at least one of the plurality of medical image data.

It is preferable that the plurality of medical image data include the medical image data having different resolutions from each other.

It is preferable that the plurality of medical image data include the medical image data subjected to different pieces of image conversion processing from each other.

It is preferable that the plurality of medical image data include the medical image data having different imaging times from each other.

It is preferable that a false negative rate of the re-detection result of the second detector be lower than a false negative rate of the detection result of the first detector.

It is preferable that the first detector be constructed in advance by training a machine learning algorithm using an initial medical image data set, and the processor train the first detector using the first medical image data set and the initial medical image data set.

It is preferable that the processor perform weighting on each of the initial medical image data set and the first medical image data set, and then train the first detector.

It is preferable that the processor perform weighting on each first medical image data set included in a plurality of the first medical image data sets, and then train the first detector.

It is preferable that the medical image data included in the first medical image data set be acquired at a specific facility.

It is preferable that the processor detect, by the first detector, the region-of-interest based on the medical image data during examination in which the medical image data is acquired, and receive the information for specifying the medical image data evaluated as false negative, during the examination.

It is preferable that the processor re-detect, by the second detector, the region-of-interest based on the medical image data during the examination.

It is preferable that the processor perform a control of displaying, on the display, the medical image data and the detection result of the region-of-interest based on the medical image data.

It is preferable that the processor receive information for specifying the medical image data evaluated that the detection result is false positive by the user, generate a second medical image data set including the medical image data evaluated as false positive and an annotation indicating that the medical image data is a region-of-non-interest, and train the first detector using the second medical image data set.

In addition, another aspect of the present invention relates to a training data generation device comprising a processor, in which the processor acquires medical image data in which an examination target is reflected, detects, by a first detector, a region-of-interest including the examination target reflected in the medical image data based on the medical image data, performs a control of displaying, on a display, the medical image data which is a detection result indicating that the region-of-interest is not detected, receives information for specifying the medical image data evaluated that the detection result is false negative by a user, re-detects, by a second detector, the region-of-interest including the examination target reflected in the medical image data based on the medical image data evaluated as false negative, generates a medical image data set including the medical image data and a re-detection result of the region-of-interest associated with the medical image data, and stores the medical image data set in a storage unit set in advance.

In addition, still another aspect of the present invention relates to a diagnosis support system comprising a processor, in which the processor acquires medical image data in which an examination target is reflected, detects, by a first detector, a region-of-interest including the examination target reflected in the medical image data based on the medical image data, performs a control of displaying, on a display, the medical image data which is a detection result indicating that the region-of-interest is not detected, receives information for specifying the medical image data evaluated that the detection result is false negative by a user, re-detects, by a second detector, the region-of-interest including the examination target reflected in the medical image data based on the medical image data evaluated as false negative, generates a medical image data set including the medical image data and a re-detection result of the region-of-interest associated with the medical image data, generates a third detector by training the first detector using the medical image data set, and generates diagnosis support information related to the examination target by detecting, by the third detector, the region-of-interest included in the examination target reflected in the medical image data based on the medical image data.

It is preferable that the first detector be the third detector constructed in the past.

According to the present invention, in a case in which the region-of-interest is detected using the medical image, it is possible to efficiently improve the detection accuracy.

DESCRIPTION OF THE PREFERRED EMBODIMENTS

Figure 1:
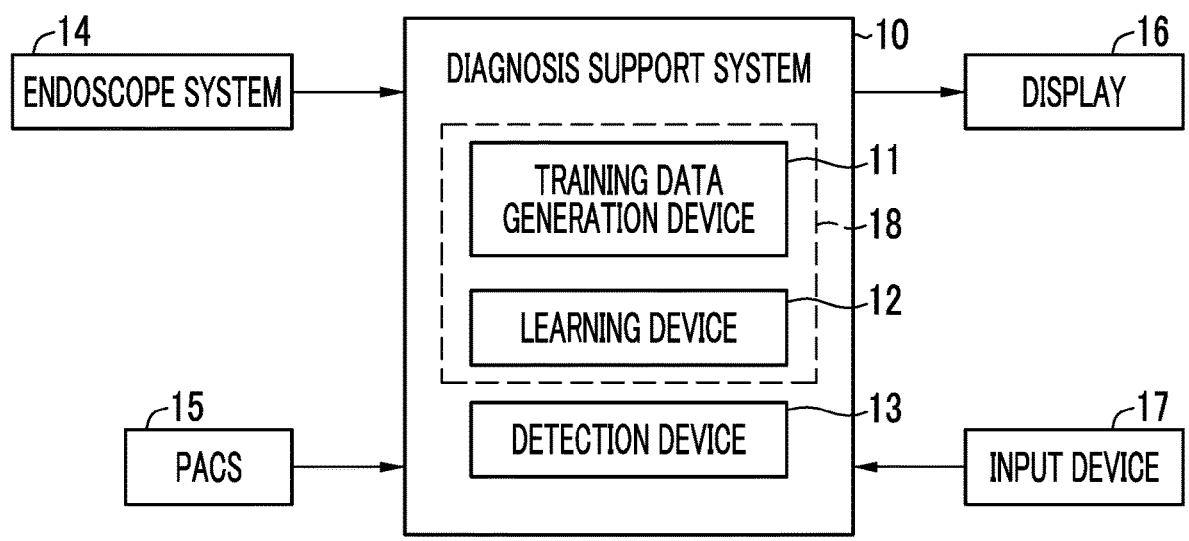
FIG. 1 is a schematic diagram of a diagnosis support system.

An example of a basic configuration of the present invention will be described. As shown in FIG. 1, a diagnosis support system 10 comprises a training data generation device 11, a learning device 12, and a detection device 13. The diagnosis support system 10 connects a device that can output medical image data, such as an endoscope system 14, various modalities (not shown) such as X-ray examination, and a picture archiving and communication system (PACS) 15, a display device, such as a display 16, and an input device 17, such as a keyboard (not shown) or a touch panel of the display 16 to each other.

The diagnosis support system 10 detects a region-of-interest included in an examination target reflected in a medical image based on the medical image data acquired from the endoscope system 14 or the like, and generates diagnosis support information related to the examination target. The diagnosis support information is output to be displayed on the display 16, for example. A doctor can use the displayed diagnosis support information as information in a case of diagnosing the examination target. It should be noted that, in the present specification, the region-of-interest is a region-of-interest in the examination target reflected in the medical image, for example, a lesion region.

The medical image data is, for example, medical image data handled by the PACS, specific examples thereof include an X-ray image by an X-ray examination, an MRI by an MR examination, a CT image by a CT examination, an endoscopic image by an endoscopic examination, and an ultrasound image by an ultrasound examination.

The training data generation device 11 comprises a first detector and a second detector, and detects the region-of-interest by the first detector based on the acquired medical image data. A user evaluates a detection result of the first detector, and the training data generation device 11 receives information for specifying the medical image data evaluated that the detection result is false negative by the user. Moreover, based on the medical image data evaluated as false negative, the second detector re-detects the region-of-interest. A first medical image data set is generated in which the medical image data evaluated as false negative and the re-detection result are associated with each other.

The learning device 12 trains the first detector using the first medical image data set generated by the training data generation device 11. The detection device 13 detects the region-of-interest included in the examination target reflected in the medical image data using a third detector constructed by the learning device 12 by training the first detector, and generates the diagnosis support information related to the examination target. It should be noted that the first detector, the second detector, and the third detector are learning models constructed using a machine learning algorithm.

As a configuration of the diagnosis support system 10, the training data generation device 11, the learning device 12, and the detection device 13 may be executed as a training data generation unit, a learning unit, and a detection unit in one computer, or the training data generation device 11, the learning device 12, and the detection device 13 may be executed by separate computers, respectively, via a network.

Figure 2:
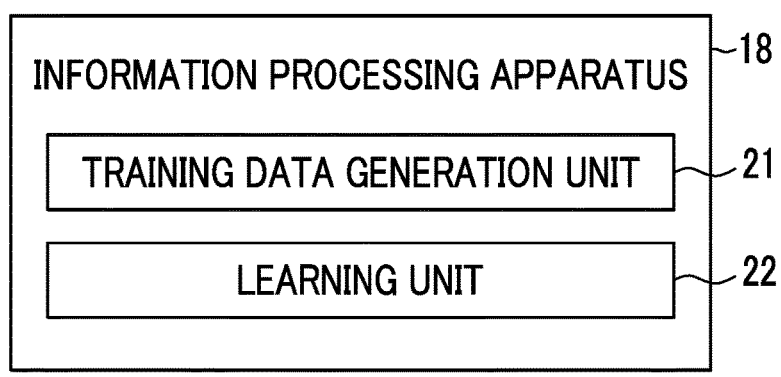
FIG. 2 is a block diagram showing a function of an information processing apparatus.

In addition, as shown in FIG. 2, as an information processing apparatus 18 comprising a training data generation unit 21 that executes a function of the training data generation device 11 and a learning unit 22 that executes a function of the learning device 12, the training data generation unit 21 and the learning unit 22 may be executed by one computer. In the present embodiment, the information processing apparatus 18 comprising the training data generation unit 21 and the learning unit 22 automatically executes the function of the training data generation device 11 and the function of the learning device 12. In this case, the diagnosis support system 10 is composed of the information processing apparatus 18 and the detection device 13.

In a case in which image recognition processing, such as detection of the region-of-interest in the medical image, is performed by the diagnosis support system 10 using the detector consisting of the learning model in the machine learning technique, the detection accuracy of the region-of-interest of by detector can be improved by training the detector using the medical image data set consisting of the medical image data effective in improving the accuracy and an annotation. The medical image data set is so-called training data used for training the detector.

It should be noted that, in the present invention, the detection accuracy in the detector means a degree of matching of the detection result of the detection of the region-of-interest by the detector performed with respect to the medical image data including the examination target with the region-of-interest in the actual examination target, and high or improved accuracy means that the degree of matching is high or improved. Specifically, in a case in which the accuracy is high, the detection sensitivity of a smaller region-of-interest is increased, more types of region-of-interest can be detected, or the region-of-interest can be detected even in a case of the medical image having a poor imaging condition.

For example, it is desired to improve the detection accuracy of the region-of-interest of the detector such that the detector installed at a facility can correctly detect the medical image data in which the region-of-interest cannot be detected correctly. In this case, the medical image data selected from the medical image data stored by a filing system possessed by the facility, such as a medical image data server such as PACS, can be used.

There are two cases in which the detector cannot appropriately detect the region-of-interest in the medical image. One case is false negative (FN) that outputs the detection result indicating that the region-of-interest is not present by the detector with respect to the medical image in which the region-of-interest is actually present, and the other case is false positive (FP) that outputs the detection result indicating that the region-of-interest is present by the detector with respect to the medical image in which the region-of-interest is not actually present. Since the detection of the region-of-interest is performed based on the medical image, it is preferable to reduce the number of false negative detection results as much as possible.

Out of the medical image data possessed by the facility, the medical image data in which the detection result of the detector is false positive can be used for training of the detector, for example, after uniformly adding the annotation, such as "background".

On the other hand, for the medical image data in which the detection result of the detector is false negative, since the region-of-interest varies in each of the medical images, the annotation cannot be added uniformly. In order to create the medical image data set of the false negative medical image data, it is necessary to add the annotation appropriately indicating the region-of-interest in each medical image. However, at the facility at which the diagnosis support system is installed, it is actually difficult for the user, such as the doctor, to appropriately add the annotation indicating the region-of-interest to each of the medical images.

In the diagnosis support system 10, the information processing apparatus 18, or the training data generation device 11, the first detector is constructed by training the machine learning algorithm, which is prepared first, using an initial medical image data set, which is the medical image data set prepared first. In order to improve the detection accuracy of the region-of-interest of the constructed first detector, a first medical image data set effective for improving the detection accuracy of the first detector is prepared, and the first detector is trained using the first medical image data set again. As a result, a parameter of the first detector is adjusted.

Examples of the first medical image data set effective for improving the detection accuracy of the first detector 61 include a first medical image data set, which fails to be detected, such that the detection result is false negative or false positive in a case in which the first detector 61 actually executes the detection.

With the diagnosis support system 10, the information processing apparatus 18, or the training data generation device 11, the medical image data in which the detection result of the first detector is false negative is re-detected by the second detector, the first medical image data set to which the re-detection result is added as the annotation is generated, and the first detector is trained using the first medical image data set as the training data. Therefore, in the first detector that has been trained using the re-detection result, the detection accuracy of the region-of-interest based on the medical image data is improved, particularly in a way of reducing the number of false negative detection results.

In addition, with the diagnosis support system 10, the information processing apparatus 18, or the training data generation device 11, the first detector can be automatically trained. Therefore, in the diagnosis support system 10 using the first detector, it is possible to efficiently improve the detection accuracy of the region-of-interest based on the medical image data.

In particular, in order to improve the detection accuracy of the region-of-interest in the first detector provided in the specific diagnosis support system 10, the information processing apparatus 18, or the training data generation device 11 already installed at the facility, the first medical image data set of the medical image data in which the detection result is actually false negative by the first detector can be prepared, and the first detector can be automatically trained using the first medical image data set again. As a result, the diagnosis support system 10 or the information processing apparatus 18 can automatically perform learning specialized in detecting the false negative medical image generated at the facility.

Therefore, with the diagnosis support system 10, the information processing apparatus 18, or the training data generation device 11, the diagnosis support system 10 installed at the facility, it is possible to automatically and efficiently improve the detection accuracy for the detection of the region-of-interest in a way of reducing the number of false negative detection results of the medical image generated at the facility. Therefore, in a case in which the region-of-interest is detected using the medical image, it is possible to efficiently improve the detection accuracy.

Figure 3:
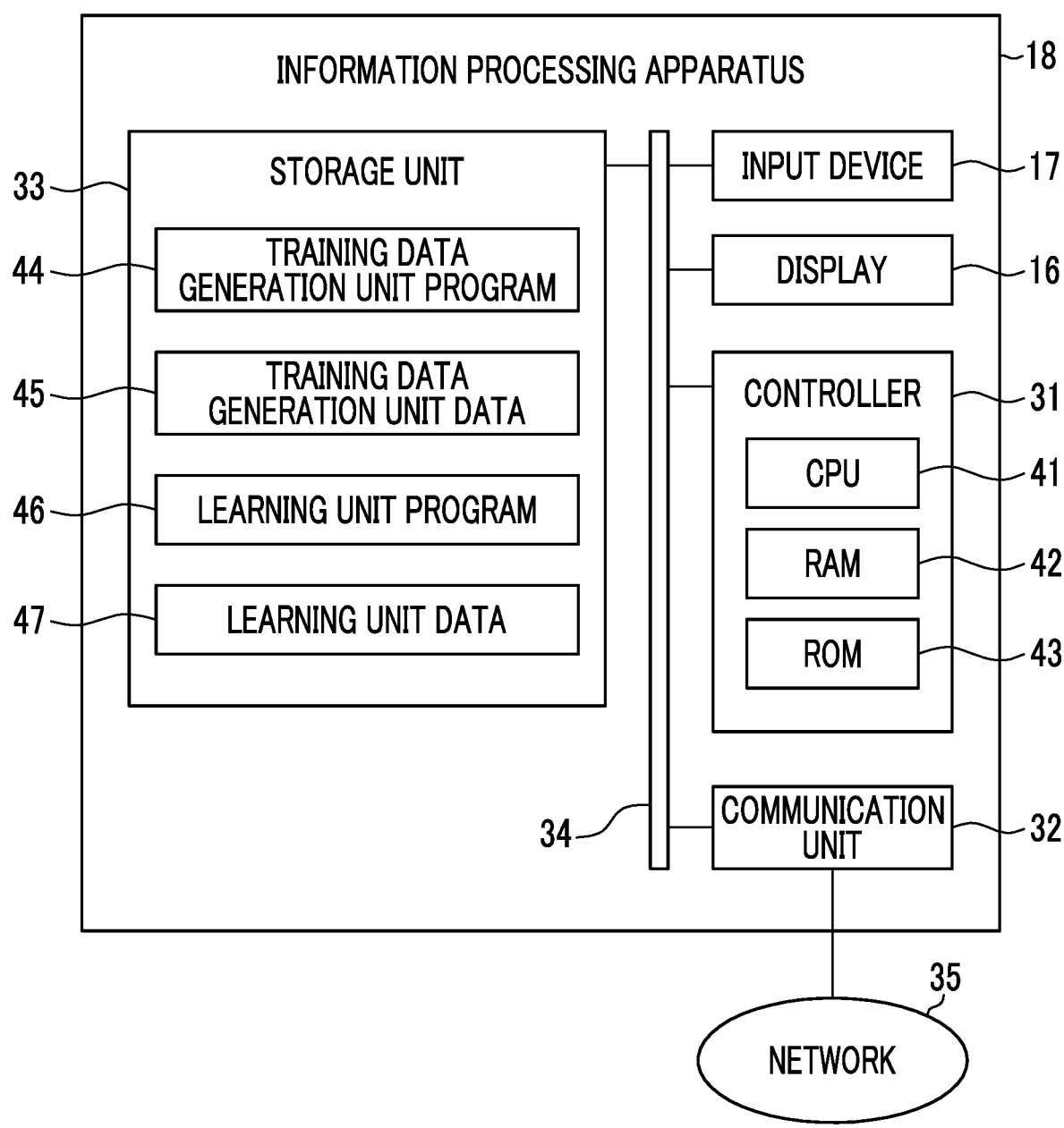
FIG. 3 is an explanatory diagram for describing a configuration of the information processing apparatus.

The information processing apparatus 18 according to the embodiment of the present invention will be described. As shown in FIG. 3, the information processing apparatus 18 according to the present embodiment is, as a hardware configuration, a computer in which the input device 17 which is an input device, the display 16 which is an output device, a controller 31, a communication unit 32, and a storage unit 33 are electrically connected to each other via a data bus 34.

The input device 17 is an input device, such as a keyboard, a mouse, or a touch panel of the display 16. The display 16 is an output device, and may be a speaker or the like. The display 16 displays various operation screens in accordance with an operation of the input device 17, such as a mouse and a keyboard. The operation screen has an operation function by a graphical user interface (GUI). The computer constituting the information processing apparatus 18 receives an input of an operation instruction from the input device 17 via the operation screens.

The controller 31 includes a central processing unit (CPU) 41, which is a processor, a random access memory (RAM) 42, and a read only memory (ROM) 43. The CPU 41 controls units of the computer in an integrated manner by loading a program stored in the storage unit 33 or the like to the RAM 42 or the ROM 43 and executing processing in accordance with the program. The communication unit 32 is a network interface that performs a transmission control of various pieces of information via a network 35. It should be noted that the RAM 42 or the ROM 43 may have the function of the storage unit 33.

The storage unit 33 is an example of a memory, and is, for example, a disk array in which a plurality of hard disk drives, solid state drives, hard disk drives, and the like built in the computer constituting the information processing apparatus 18 or connected via a cable or a network are mounted. The storage unit 33 stores a control program, various application programs, various data for use in these programs, display data of various operation screens incidental to these programs, and the like.

The storage unit 33 according to the present embodiment stores various data such as a training data generation unit program 44, training data generation unit data 45, a learning unit program 46, and learning unit data 47.

The training data generation unit program 44 or the training data generation unit data 45 is a program or data for performing various functions of the training data generation unit 21 (see FIG. 3). The function of the training data generation unit 21 is realized by the training data generation unit program 44 and the training data generation unit data 45. In addition, in the training data generation unit data 45, the data transitorily generated by the training data generation unit program 44, such as the first medical image data set (see FIG. 7) generated by the training data generation unit 21, which will be described below, is also transitorily stored.

The learning unit program 46 or the learning unit data 47 is a program or data for performing various functions of the learning unit 22 (see FIG. 2), respectively. The function of the learning unit 22 is realized by the learning unit program 46 and the learning unit data 47. In addition, the learning unit data 47 also stores data or the like transitorily generated by the learning unit 22.

The computer constituting the information processing apparatus 18 can be a general-purpose server device, a personal computer (PC), or the like, in addition to a device designed exclusively for the information processing apparatus 18.

Figure 4:
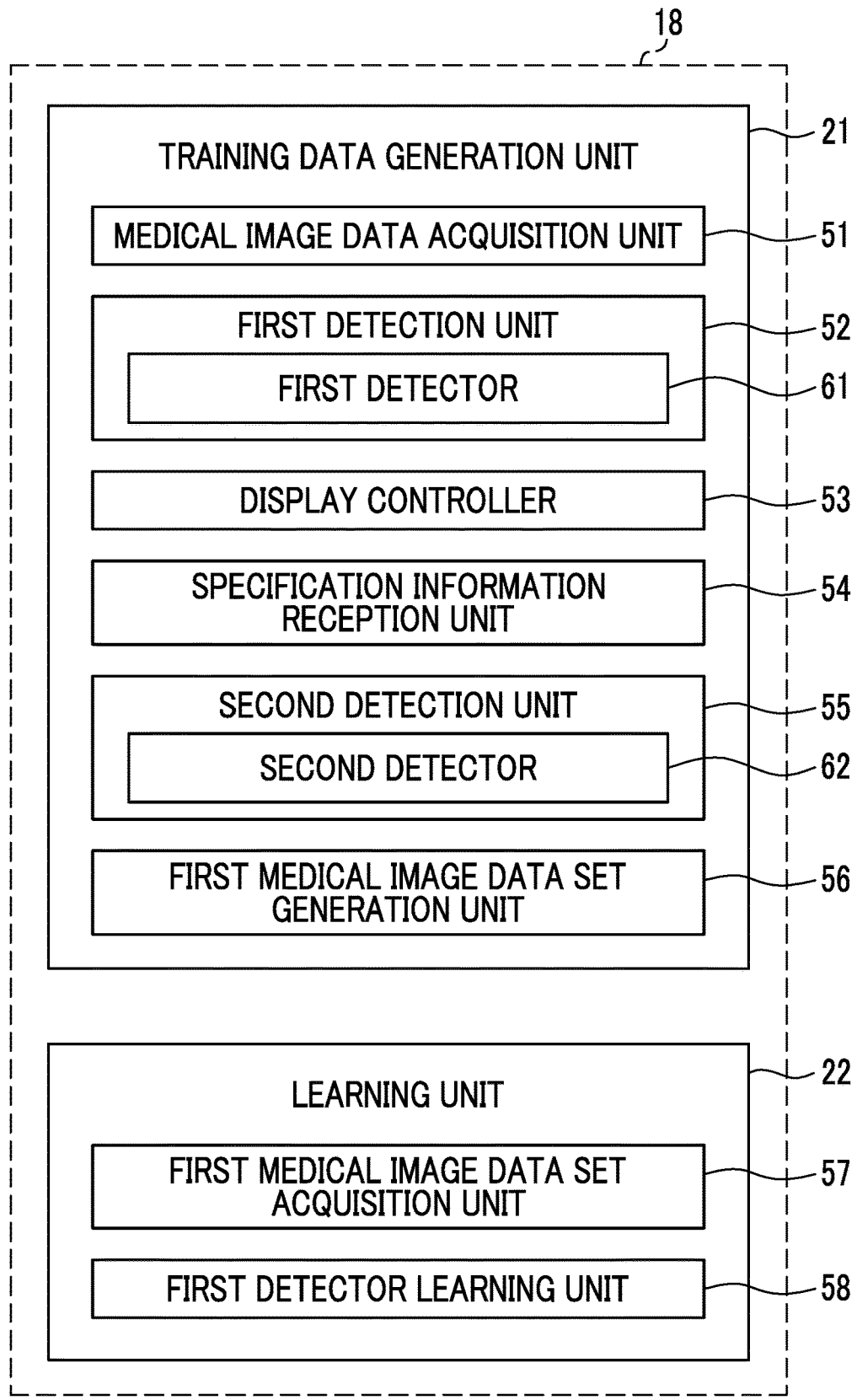
FIG. 4 is a block diagram showing functions of a training data generation unit and a learning unit provided in the information processing apparatus.

As shown in FIG. 4, the information processing apparatus 18 according to the present embodiment comprises the training data generation unit 21 and the learning unit 22 as a software configuration (see FIG. 2), and the training data generation unit 21 comprises a medical image data acquisition unit 51, a first detection unit 52, a display controller 53, a specification information reception unit 54, a second detection unit 55, and a first medical image data set generation unit 56. The learning unit 22 comprises a first medical image data set acquisition unit 57 and a first detector learning unit 58.

The information processing apparatus 18 according to the present embodiment is a processor device, and the information processing apparatus 18 stores a program related to medical image data processing in the storage unit 33 which is a program memory. In the information processing apparatus 18, by operating the program in the program memory by the controller 31 composed of the processor and the like, the functions of the medical image data acquisition unit 51, the first detection unit 52, the display controller 53, the specification information reception unit 54, the second detection unit 55, and the first medical image data set generation unit 56 of the training data generation unit 21, and the first medical image data set acquisition unit 57 and the first detector learning unit 58 of the learning unit 22 are realized.

The training data generation unit 21 detects the region-of-interest by the first detector based on the acquired medical image data, re-detects the region-of-interest based on the specific medical image data, and generates the first medical image data set to which the re-detection result of the re-detected region-of-interest and the medical image data are associated with each other. The learning unit 22 trains the detector using the generated first medical image data set.

Figure 5:
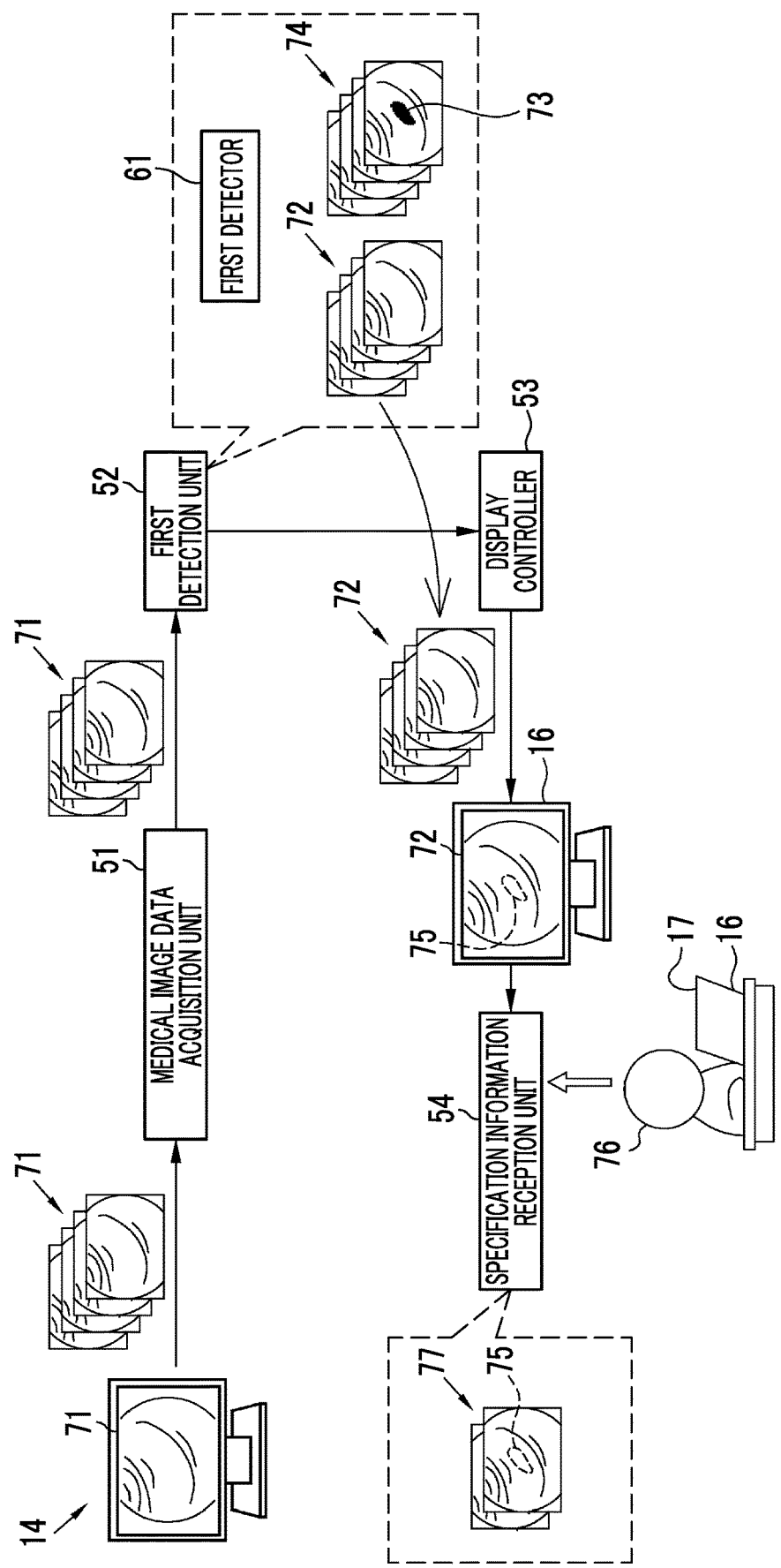
FIG. 5 is an explanatory diagram for describing a flow of processing including a first detection unit.

As shown in FIG. 5, the medical image data acquisition unit 51 provided in the training data generation unit 21 acquires the medical image data in which the examination target in the endoscopic examination is reflected, from the device that can output the medical image data, such as the endoscope system 14. In the present embodiment, the endoscopic image data 71 acquires endoscopic image data 71 captured during the examination from the endoscope system 14 as the medical image in real time. Therefore, as the description of the present embodiment, in the following, a case will be described in which the endoscopic image data 71 is used as the medical image data.

The first detection unit 52 includes a first detector 61, and the first detector 61 detects the region-of-interest included in the examination target reflected in the endoscopic image data 71 based on the acquired endoscopic image data 71. The first detector 61 is specifically a learning model constructed using a machine learning algorithm, and is a learning model that can output the presence or absence of the region-of-interest in the endoscopic image data 71 as an objective variable in a case in which a feature amount based on the endoscopic image data 71 is input to the first detector 61. The first detector 61 is trained in advance using the machine learning algorithm using an initial image data set for the first detector 61 consisting of the endoscopic image data such that the presence or absence of the region-of-interest in the endoscopic image data 71 can be output as an objective variable, and the parameter is adjusted.

As the machine learning algorithm used for the first detector 61, various algorithms can be used as long as the algorithms are used for supervised learning, but it is preferable to use an algorithm that outputs a good inference result as an objective variable in image recognition. For example, it is preferable to use a multi-layer neural network or a convolutional neural network, and it is preferable to use a method called so-called deep learning.

The detection result of the region-of-interest includes a position, a size or area, a shape, or the number of the regions-of-interest detected in the endoscopic image data 71, and also includes a content indicating that the position or the size of the region-of-interest is 0, that is, the region-of-interest is not detected. Based on the detection result of the region-of-interest by the first detector 61, the endoscopic image data 71 is classified into region-of-interest non-detection endoscopic image data 72 (first medical image data) in which a region-of-interest 73 is not detected, and region-of-interest detection endoscopic image data 74 in which the region-of-interest 73 is detected. It should be noted that, although a plurality of two or more regions-of-interest may be detected in one endoscopic image, the region-of-interest non-detection endoscopic image data 72 is the endoscopic image data 71 in which the region-of-interest is not detected at all. The region-of-interest detection endoscopic image data 74 is associated with the detection result of the region-of-interest, and can be used as the diagnosis support information for a doctor 76 to diagnose the examination target.

The display controller 53 performs a control of displaying, on the display 16, the endoscopic image data 71, which has the detection result indicating that the region-of-interest is not detected, that is, the region-of-interest non-detection endoscopic image data 72. In the region-of-interest non-detection endoscopic image data 72, a non-detection region-of-interest 75 that is not detected by the first detector 61 but has a possibility of being determined as the region-of-interest in a case in which the doctor makes a confirmation may be included. It should be noted that, the display controller 53 may perform a control of at least displaying the region-of-interest non-detection endoscopic image data 72 and displaying the endoscopic image data 71 other than the region-of-interest non-detection endoscopic image data 72, and may perform a control of displaying the region-of-interest detection endoscopic image data 74.

The doctor 76 who is the user determines whether or not the non-detection region-of-interest 75 is included, from the region-of-interest non-detection endoscopic image data 72 displayed on the display 16. Out of the region-of-interest non-detection endoscopic image data 72, the endoscopic image data 71 determined by the doctor 76 to include the non-detection region-of-interest 75 is false negative endoscopic image data 77 (second medical image data) in which the detection result by the first detector 61 is false negative. The doctor 76 determines the presence or absence of the non-detection region-of-interest 75 from the region-of-interest non-detection endoscopic image data 72, makes a determination that it is the false negative endoscopic image data 77 in a case in which the non-detection region-of-interest 75 is included, and selects the endoscopic image data 71 which is the false negative endoscopic image data 77 by the input device 17, such as a touch panel of the display 16.

The specification information reception unit 54 receives information for specifying the endoscopic image data 71 which includes the non-detection region-of-interest 75 and is the false negative endoscopic image data 77 evaluated that the detection result is false negative by the doctor 76, based on the selection by the doctor 76 using the input device 17.

Figure 6:
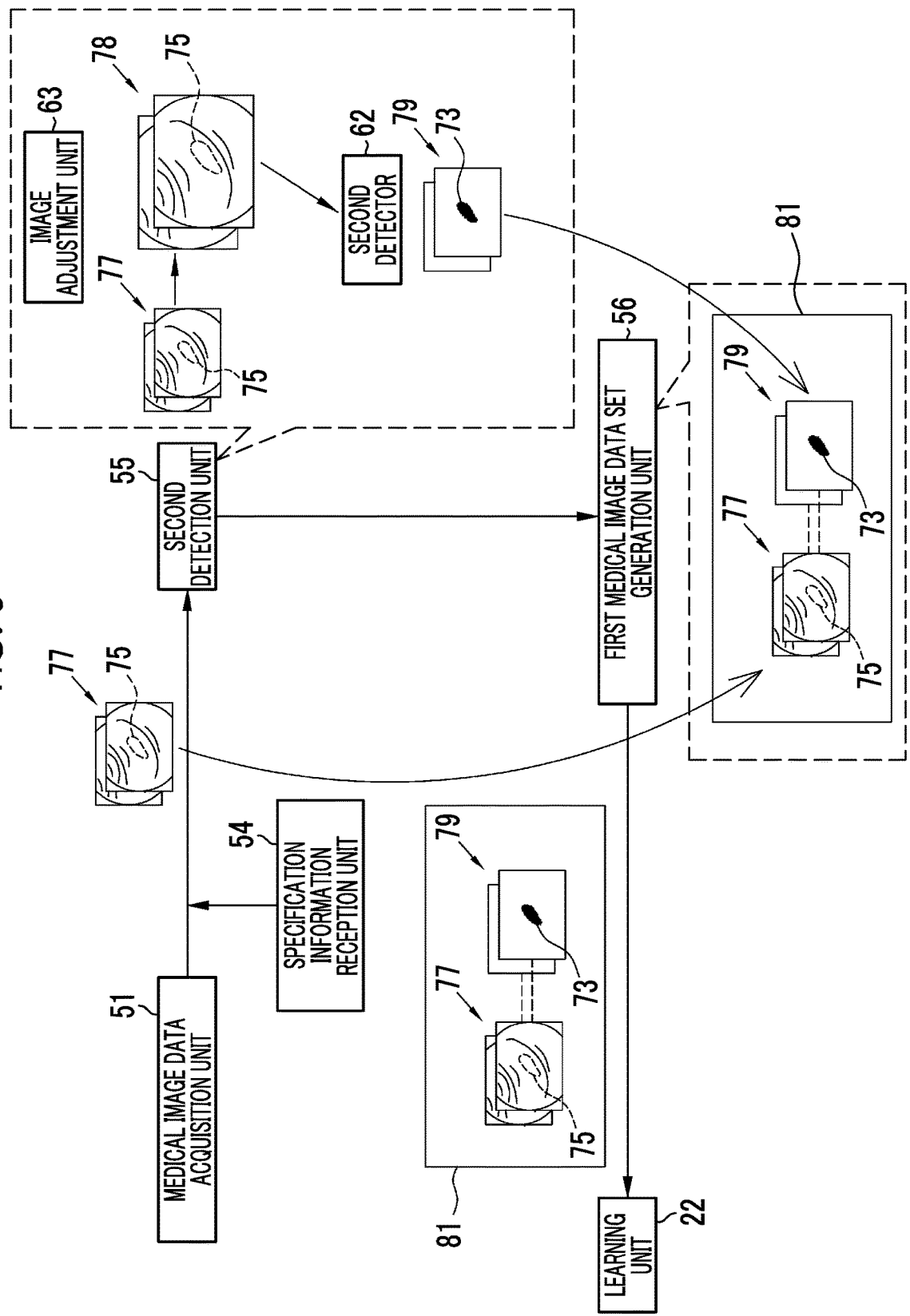
FIG. 6 is an explanatory diagram for describing a flow of processing including a second detection unit.

As shown in FIG. 6, the second detection unit 55 specifies and acquires the false negative endoscopic image data 77 from the endoscopic image data 71 acquired by the medical image data acquisition unit 51, from the information for specifying the false negative endoscopic image data 77 from the specification information reception unit 54.

The second detection unit 55 re-detects the region-of-interest 73 included in the examination target reflected in the false negative endoscopic image data 77 based on the false negative endoscopic image data 77. The second detection unit 55 includes a second detector 62. The second detector 62 is specifically a learning model constructed using a machine learning algorithm, and is a learning model that can output, as a re-detection result 79, the presence or absence of the region-of-interest 73 in the false negative endoscopic image data 77 as an objective variable in a case in which a feature amount based on the false negative endoscopic image data 77 is input to the second detector 62.

As the feature amount based on the false negative endoscopic image data 77, a feature amount in a case in which the false negative endoscopic image data 77, which is the same type of endoscopic image data 71 as a case of being used for the first detector 61, is used may be used, and a feature amount of an adjusted endoscopic image 78 generated by performing the image adjustment processing on the false negative endoscopic image data 77 may be used. In addition, the false negative endoscopic image data 77 may be used alone, or a plurality of endoscopic image data 71 including the false negative endoscopic image data 77 and other endoscopic image data 71 may be used.

As a method of image adjustment processing, the image adjustment processing can be performed to improve the detection accuracy of the learning model in the machine learning technique, and examples thereof include a method in which the adjusted endoscopic image 78 created by changing the resolution is used. In addition, similarly, as a method using a plurality of false negative endoscopic image data 77, a method performed to improve the detection accuracy of the learning model in the machine learning technique can be adopted, examples thereof include a method in which the adjusted endoscopic image 78 is used in which the false negative endoscopic image data 77 is duplicated and the respective resolutions are different from each other, and a method in which the endoscopic image data 71 of frames before and after the false negative endoscopic image data 77 is acquired is used as the adjusted endoscopic image 78.

Figure 7:
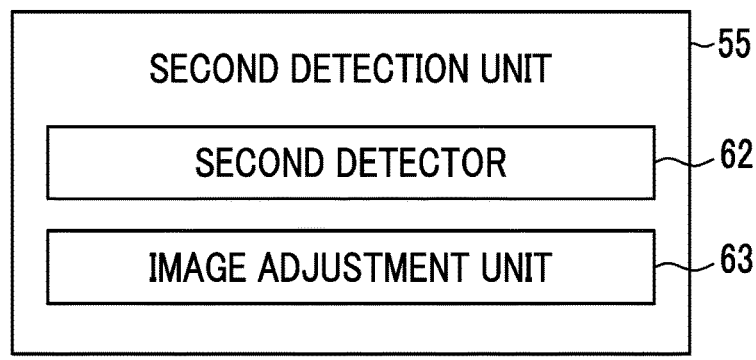
FIG. 7 is a block diagram showing a function of the second detection unit.

As shown in FIG. 7, in the present embodiment, the second detection unit 55 comprises an image adjustment unit 63. The image adjustment unit 63 performs image adjustment processing of increasing the resolution of the false negative endoscopic image data 77, and generates the adjusted endoscopic image 78. It is preferable that the second detector 62 re-detect the region-of-interest based on the endoscopic image data 71 having a high resolution as compared with the first detector 61. By inputting endoscopic image data having a high resolution to the second detection unit 55, it is possible to improve the detection sensitivity of a smaller region-of-interest.

As a method of image adjustment processing of increasing the resolution of the false negative endoscopic image data 77, various methods performed in the related art to increase the number of pixels of the image data can be adopted. After performing the method of increasing the number of pixels, image processing, such as sharpness processing, may be performed.

As shown in FIG. 6, the second detector 62 re-detects the region-of-interest 73 in the adjusted endoscopic image 78 by inputting the feature amount using the adjusted endoscopic image 78 subjected to the image adjustment processing. The second detector 62 is a detector that can re-detect the region-of-interest 73 that cannot be correctly detected by the first detector 61. Therefore, the second detector 62 is a detector different from the first detector 61. The second detector 62 is trained using an initial image data set for the second detector 62 consisting of endoscopic image data using the machine learning algorithm, and the parameter is adjusted such that the region-of-interest that cannot be correctly detected by the first detector 61 can be re-detected.

The machine learning algorithm used for the second detector 62 may be the same as or different from the first detector 61, and various algorithms can be used as long as the algorithms are used for supervised learning, but it is preferable to use an algorithm that outputs a good inference result as an objective variable in image recognition. For example, it is preferable to use a multi-layer neural network or a convolutional neural network, and it is preferable to use a method called so-called deep learning.

The re-detection result 79 of the region-of-interest includes a position, a size or area, a shape, or the number of the regions-of-interest 73 re-detected in the false negative endoscopic image data 77, and also includes the re-detection result 79 in which the region-of-interest 73 is not re-detected. The re-detection result 79 of the region-of-interest 73 can be the annotation for the false negative endoscopic image data 77. In addition, the false negative endoscopic image data 77 is associated with the re-detection result 79 related to the region-of-interest, and the re-detection result 79 itself can be used as the diagnosis support information for the doctor 76 to diagnose the examination target.

The first medical image data set generation unit 56 generates a first medical image data set 81 including the false negative endoscopic image data 77 input to the second detector 62 and the re-detection result 79 of the region-of-interest 73 associated with the false negative endoscopic image data 77.

In the present specification, in the association in a case of the re-detection result 79 of the region-of-interest 73 associated with the false negative endoscopic image data 77, the re-detection result 79 detected based on the false negative endoscopic image data 77 can be specified in a case in which the false negative endoscopic image data 77 is specified. For the association, for example, correspondence information in which the false negative endoscopic image data 77 and the re-detection result 79 detected based on the false negative endoscopic image data 77 correspond to each other can be used. By the correspondence information, in a case in which the false negative endoscopic image data 77 is specified, the re-detection result 79 of the false negative endoscopic image data 77 is specified. In the present embodiment, the correspondence information in which the false negative endoscopic image data 77 and the re-detection result 79 detected based on the false negative endoscopic image data 77 correspond to each other is created and used. The correspondence information may be information in which the feature amount of the false negative endoscopic image data 77 and the re-detection result 79 associated with each other.

The first medical image data set 81 can be the training data for training the first detector 61. The first medical image data set 81 is transmitted to the learning unit 22.

Figure 8:
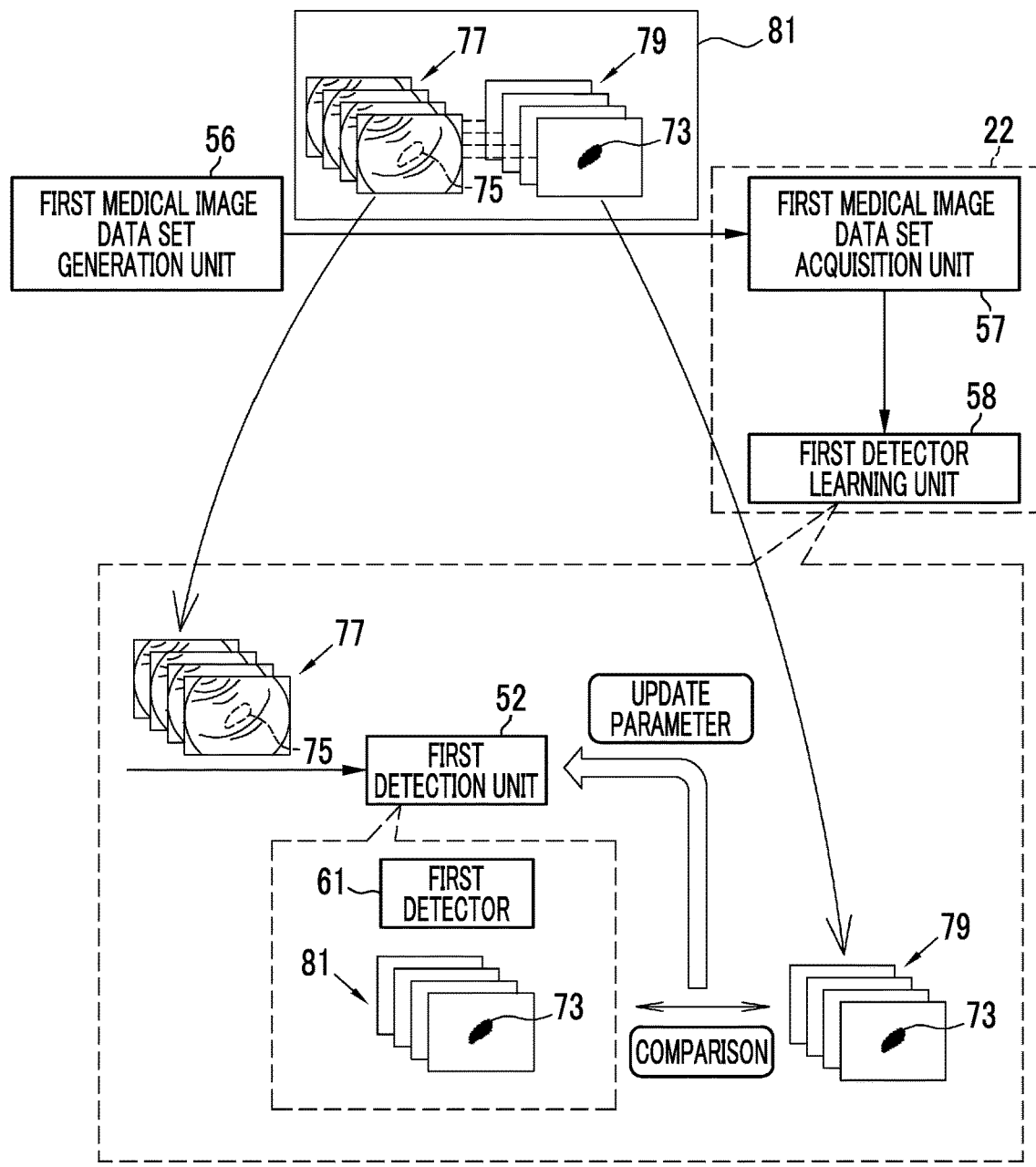
FIG. 8 is an explanatory diagram for describing a flow of processing including the learning unit.

As shown in FIG. 8, in the learning unit 22, the first medical image data set acquisition unit 57 acquires the first medical image data set 81 generated by the first medical image data set generation unit 56. The first detector learning unit 58 trains the first detection unit 52 using the first medical image data set 81 as the training data. The first medical image data set 81, which is the training data, the false negative endoscopic image data 77 input to the first detector 61 in a case of learning, and the re-detection result 79 for the false negative endoscopic image data 77, which is the annotation.

The learning is supervised learning, and teacher data (annotation) is the re-detection result 79 of the region-of-interest 73 in the false negative endoscopic image data 77. The first detector learning unit 58 inputs the false negative endoscopic image data 77 to the first detector 61, and compares an output detection result 91 with the re-detection result 79, which is the annotation. Moreover, the parameter of the first detector 61 is updated such that the detection result 91 is the same as the re-detection result 79.

The first detector learning unit 58 can adopt various methods performed by the machine learning technique in a case of learning. For example, in a case in which an algorithm of the first detector 61 is a neural network, it is preferable to perform learning such that a part of network parameters is fixed and a part of network parameters is updated. As a result, it is possible to prevent so-called catastrophic forgetting, and it is possible to handle the new endoscopic image data 71 while maintaining a basic performance of the first detector 61 before the first detector 61 is trained using the first medical image data set 81. In addition, for the same reason, it is also preferable to reduce a learning rate which is a hyperparameter.

As described above, with the information processing apparatus 18, the false negative endoscopic image data 77 in which the detection result of the first detector 61 is false negative is re-detected by the second detector, the first medical image data set in which the re-detection result 79 is added as the annotation is generated, and the first detector 61 is trained using the first medical image data set as the training data. Therefore, in the first detector 61 that has been trained using the re-detection result 79, the detection accuracy of the region-of-interest based on the endoscopic image data 71 is improved, particularly in a way of reducing the number of false negative detection results.

In addition, with the information processing apparatus 18, since it is possible to automatically perform learning without human intervention except for selecting the false negative endoscopic image data 77 by the user, in the information processing apparatus 18 using the first detector 61, it is possible to efficiently improve the detection accuracy of the region-of-interest 73 based on the endoscopic image data 71.

In particular, in order to improve the detection accuracy of the region-of-interest in the first detector 61 provided in the specific information processing apparatus 18 already installed at the facility, the first medical image data set 81 of the endoscopic image data 71 in which the detection result is actually false negative by the first detector 61 can be prepared, and the first detector 61 can be automatically trained using the first medical image data set 81 again. As a result, the information processing apparatus 18 can automatically perform learning specialized in detecting the endoscopic image data 71, which is false negative and generated at the facility.

Therefore, with the information processing apparatus 18, the diagnosis support system 10 installed at the facility, it is possible to automatically improve the detection accuracy for the detection of the region-of-interest in a way of reducing the number of false negative detection results of the endoscopic image data 71 generated at the facility.

Then, the first detector 61 and the second detector 62 will be further described. The second detector 62 is a detector different from the first detector 61, and is a detector that can re-detect the region-of-interest for the endoscopic image data 71 in which the region-of-interest is not detected by the first detector 61 and the detection result is false negative. The second detector 62 re-detects the region-of-interest by processing with higher accuracy than the processing in the first detector 61.

Generally, in the learning model that detects the region-of-interest, the detection accuracy and the detection speed, that is, a small amount of calculation, are in a trade-off relationship, and the second detector 62 performs the processing that requires a larger amount of calculation than the first detector 61. For example, it is preferable to suppress the amount of calculation such that the region-of-interest can be detected in real time during the endoscopic examination in the processing in the first detector 61, but the processing in the second detector 62 can be performed in the background after the endoscopic examination or during the endoscopic examination, so that it is unlikely to cause a problem as a whole even in a case in which it takes a lot of calculation time.

Therefore, it is preferable that an operation load of the second detector 62 be higher than an operation load of the first detector 61. A high operation load means that the amount of calculation is large in the controller 31 composed of the processor or the like. The second detector 62 has a larger amount of calculation than the processing in the first detector 61 and performs processing with high accuracy, so that it is possible to easily re-detect the region-of-interest that is not detected in the first detector 61.

In addition, it is preferable that the second detector 62 be constructed using the machine learning algorithm, and the number of parameters of the second detector 62 be larger than the number of parameters of the first detector 61. Therefore, it is preferable that the controller 31 set the number of parameters of the first detector 61 to be less than the number of parameters of the second detector 62. As the machine learning algorithm, as described above, it is preferable to use a multi-layer neural network or a convolutional neural network that is used for supervised learning and outputs good inference result as an objective variable in image recognition, and it is preferable to use a method called so-called deep learning. For example, in these algorithms, the learning model having a large number of parameters can perform the image recognition with high accuracy. Therefore, in the second detector 62, the region-of-interest that is not detected by the first detector 61 can be easily re-detected.

In addition, since it is a model for detecting the region-of-interest, an algorithm used for object detection can be used as the learning model for the second detector 62. In particular, in the object detection, it is preferable to use an algorithm called a two-stage system that can detect an object with high accuracy. The two-stage system algorithm is an algorithm that performs detection in two stages, and is an algorithm that executes a stage of detecting a candidate for a region of the subject and a stage of identifying a category of the candidate for the region in series. For example, the two-stage system algorithm generally has a higher operation load and is operated at a lower speed than a single-stage system algorithm that performs region extraction and category identification at the same stage. However, as described above, since it is preferable that the second detector 62 have a higher operation load than the first detector 61, it is preferable that the second detector 62 use the two-stage system algorithm, which enables the re-detection of the region-of-interest with higher accuracy.

Regarding the endoscopic image data 71 input to the second detector 62 and the first detector 61, it is preferable that the second detector 62 re-detect the region-of-interest based on each of a plurality of endoscopic image data 71, and integrate a plurality of the re-detection results based on the plurality of endoscopic image data 71 into the re-detection result by the second detector 62. By using a plurality of re-detection results 79 obtained by inputting the plurality of endoscopic image data 71, it is possible to detect the region-of-interest of the endoscopic image data 71 with high accuracy. Therefore, in the second detector 62, the region-of-interest that is not detected by the first detector 61 can be easily re-detected.

Figure 9:
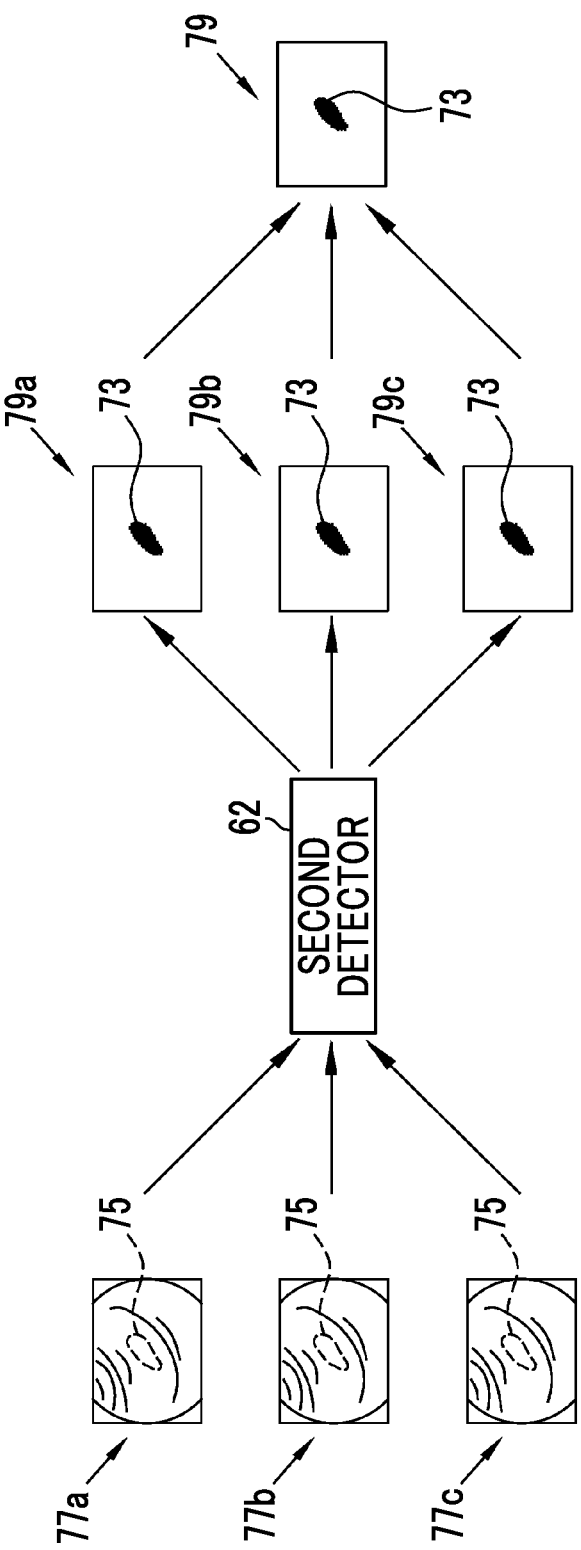
FIG. 9 is an explanatory diagram for describing processing of a second detector.

As shown in FIG. 9, by inputting, as the plurality of endoscopic image data 71, each of false negative endoscopic image data 77a, false negative endoscopic image data 77b, and false negative endoscopic image data 77c to the second detector 62, a re-detection result 79a, a re-detection result 79b, and a re-detection result 79c are obtained. These plurality of re-detection results are integrated into the re-detection result 79 by the second detector 62.

As a method of integrating the re-detection result 79a, the re-detection result 79b, and the re-detection result 79c, which are the plurality of re-detection results 79, a method performed in the related art, such as various method in which the image data using the re-detection result 79a, the re-detection result 79b, and the re-detection result 79c are used as the image data to integrate the image data, can be adopted. For example, the integrated re-detection result 79 can be obtained by performing averaging or majority decision on the pixel values at the same position in each of the re-detection result 79a, the re-detection result 79b, and the re-detection result 79c. In this case, the image data of the re-detection result 79a, the re-detection result 79b, and the re-detection result 79c may be integrated after registration.

In addition, regarding the endoscopic image data 71 input to the second detector 62 and the first detector 61, a plurality of the second detectors 62 may be present, and each of the second detectors 62 may re-detect the region-of-interest based on at least one of the plurality of endoscopic image data 71 and may integrate the plurality of re-detection results into the re-detection result by the second detector 62. By using the plurality of re-detection results 79 obtained by the plurality of second detectors 62, it is possible to detect the region-of-interest of the endoscopic image data 71 with high accuracy. Therefore, in the second detector 62, the region-of-interest that is not detected by the first detector 61 can be easily re-detected.

Figure 10:
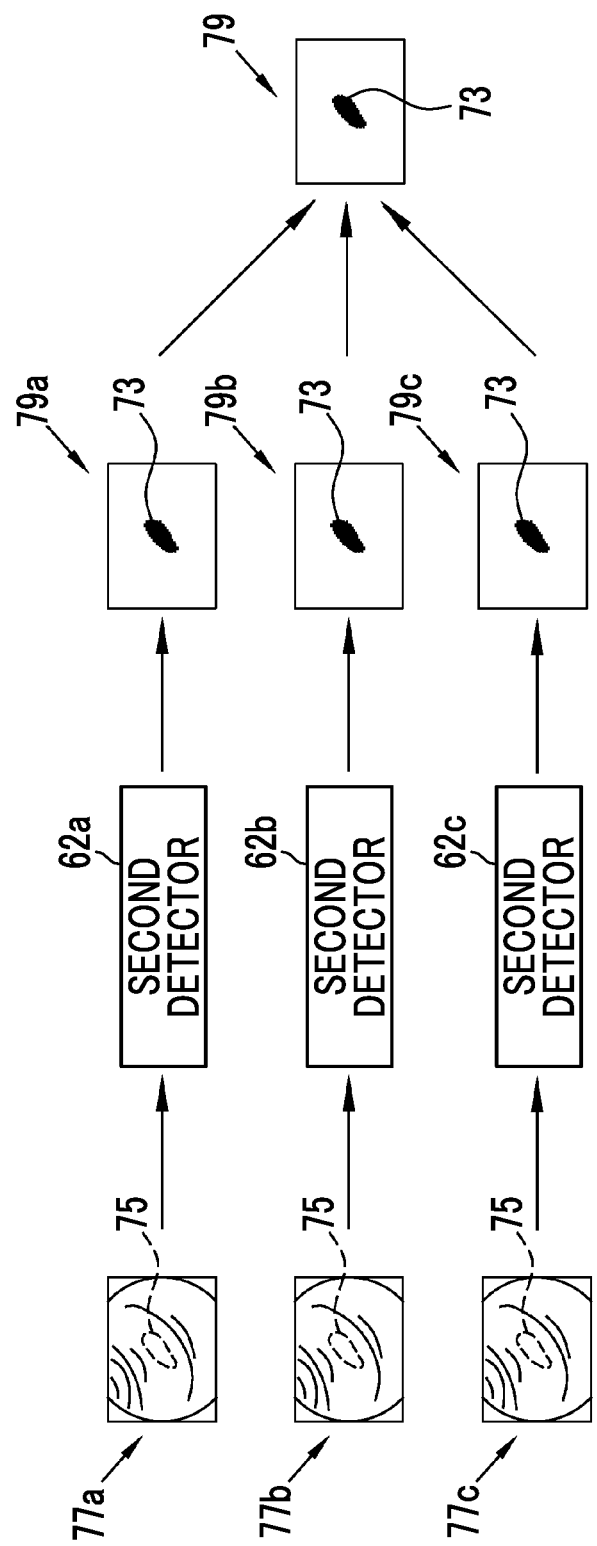
FIG. 10 is an explanatory diagram for describing processing of a plurality of second detectors.

As shown in FIG. 10, as the second detector 62, each of a second detector 62a, a second detector 62b, and a second detector 62c may re-detect the region-of-interest based on at least one of the plurality of endoscopic image data 71 and may integrate the plurality of re-detection results into the re-detection result by the second detector 62. Specifically, the second detector 62a outputs the re-detection result 79a by re-detecting the region-of-interest based on the false negative endoscopic image data 77a, the second detector 62b outputs the re-detection result 79b by re-detecting the region-of-interest based on the false negative endoscopic image data 77b, and the second detector 62c outputs the re-detection result 79c by re-detecting the region-of-interest based on the false negative endoscopic image data 77c.

The method of integrating the plurality of re-detection results 79 is the same as described above. An integrated re-detection result 79d obtained by performing averaging or majority decision on the pixel values at each position of the re-detection result 79a, the re-detection result 79b, and the re-detection result 79c is used as the re-detection result 79 by the second detector 62.

It should be noted that, as the plurality of endoscopic image data 71 input to the second detector 62, it is preferable that the plurality of endoscopic image data 71 be different from each other. By using the plurality of re-detection results 79 different from each other obtained by inputting the plurality of endoscopic image data 71, it is possible to detect the region-of-interest of the endoscopic image data 71 with high accuracy. Therefore, in the second detector 62, the region-of-interest that is not detected by the first detector 61 can be easily re-detected. Specifically, such plurality of endoscopic image data 71 can be the following endoscopic image data 71.

It is preferable that the plurality of endoscopic image data 71 include the endoscopic image data 71 having different resolutions from each other. Therefore, as described above, the image adjustment unit 63 (see FIG. 6) performs the image adjustment processing such that the plurality of false negative endoscopic image data 77 having different resolutions from each other are generated based on the false negative endoscopic image data 77, which is the endoscopic image data 71.

Figure 11:
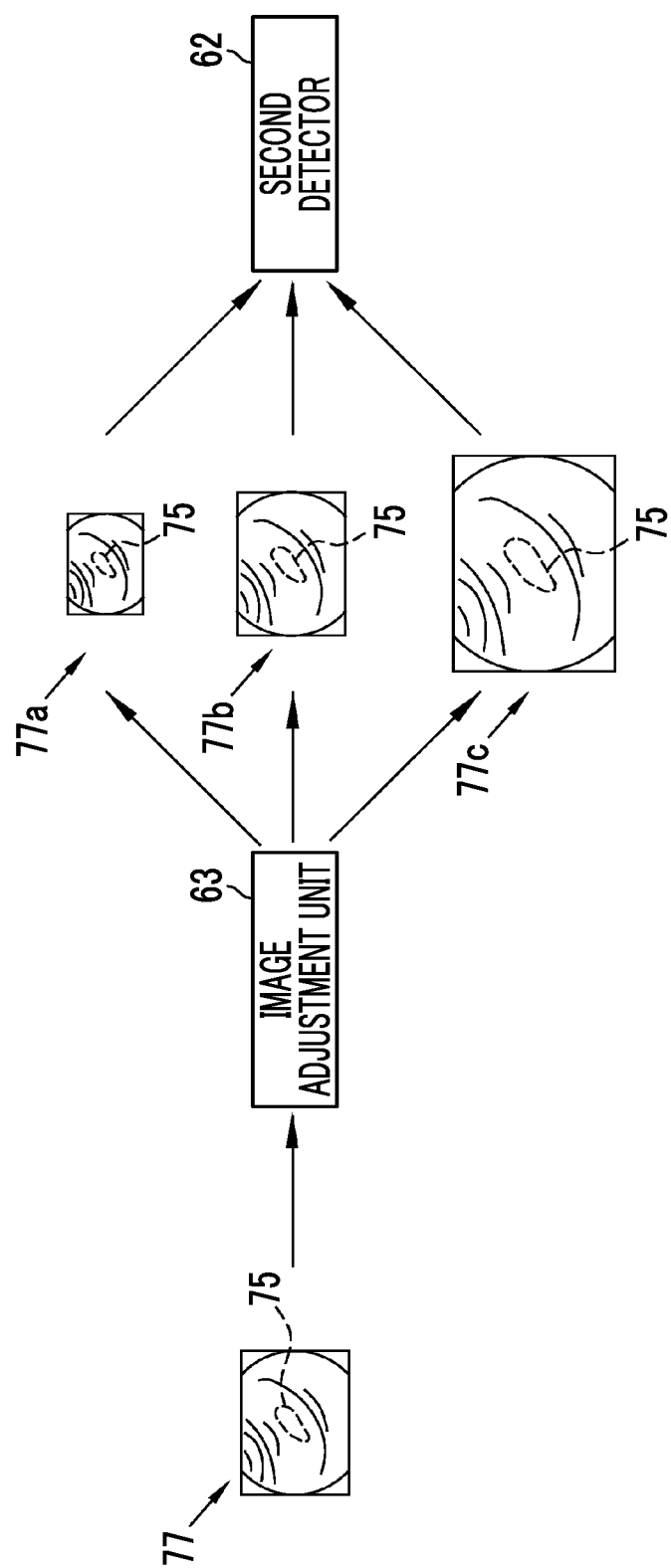
FIG. 11 is an explanatory diagram for describing processing of generating endoscopic image data having different resolutions by an image adjustment unit.

As shown in FIG. 11, the image adjustment unit 63 acquires the false negative endoscopic image data 77, and generates the false negative endoscopic image data 77a, the false negative endoscopic image data 77b, and the false negative endoscopic image data 77c, which have different resolutions from each other. In FIG. 11, a difference in size between the false negative endoscopic image data 77a, the false negative endoscopic image data 77b, and the false negative endoscopic image data 77c represents a difference in resolution. The false negative endoscopic image data 77 is, in ascending order of resolutions, the false negative endoscopic image data 77a, the false negative endoscopic image data 77b, and the false negative endoscopic image data 77c.

As described above, the second detector 62 outputs the re-detection result 79a by inputting the false negative endoscopic image data 77a, outputs the re-detection result 79b by inputting the false negative endoscopic image data 77b, and outputs the re-detection result 79c by inputting the false negative endoscopic image data 77c (see FIG. 9). The re-detection result 79a, the re-detection result 79b, and the re-detection result 79c are integrated to generate the re-detection result 79.

It should be noted that, since these re-detection results 79 are image data having different resolutions, in a case of integration, the resolution is changed to be the same as the original false negative endoscopic image data 77 before the resolution is changed by the image adjustment processing. Therefore, the resolutions of the re-detection result 79a, the re-detection result 79b, and the re-detection result 79c are made to be the same as the original resolution of the false negative endoscopic image data 77, and then an average of these re-detection results of the re-detection result 79a, the re-detection result 79b, and the re-detection result 79c is used as the re-detection result 79. As a result, the re-detection result 79 based on various types of false negative endoscopic image data 77 can be obtained, and the detection accuracy is improved by integrating these re-detection results 79. Therefore, in the second detector 62, the region-of-interest that is not detected by the first detector 61 can be easily re-detected.

The image adjustment unit 63 (see FIG. 6) may perform the image adjustment processing such that the plurality of false negative endoscopic image data 77 subjected to different pieces of image conversion processing from each other are generated based on the false negative endoscopic image data 77, which is the endoscopic image data 71.

Figure 12:
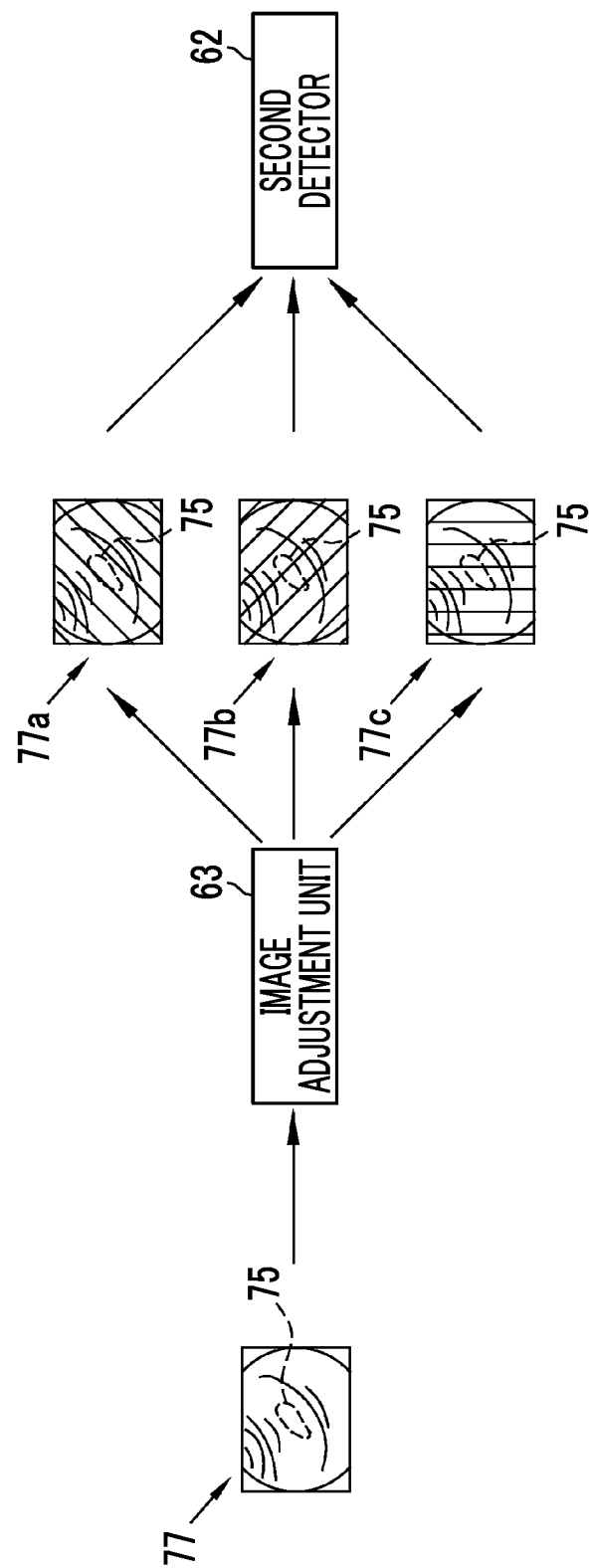
FIG. 12 is an explanatory diagram for describing processing of performing different pieces of image adjustment processing by the image adjustment unit.

As shown in FIG. 12, the image adjustment unit 63 acquires the false negative endoscopic image data 77, and generates the false negative endoscopic image data 77a, the false negative endoscopic image data 77b, and the false negative endoscopic image data 77c, which are subjected to different pieces of image conversion processing from each other. In FIG. 12, a difference in hatching between the false negative endoscopic image data 77a, the false negative endoscopic image data 77b, and the false negative endoscopic image data 77c represents a difference in performed image conversion processing.

As the image conversion processing, various pieces of image conversion processing can be adopted, but it is preferable to adopt processing of making the endoscopic image data 71 easier to see. This is because it is possible to improve the detection accuracy by inputting the endoscopic image data 71, which has a poor imaging condition, to the second detector 62 after performing processing of making the endoscopic image data 71 easier to see. Examples of the processing of making the endoscopic image data 71 easier to see include processing of changing the color, structure enhancement processing, and contrast flattening.

In addition, as the image conversion processing, it is also preferable to adopt the image conversion processing of improving the detection accuracy in the image recognition processing in machine learning. As such image conversion processing, various methods performed for augmentation of image data to increase the training data can be adopted.

In particular, it is preferable to adopt a method such as test time augmentation (TTA), which is a method considered to have excellent detection accuracy. In the TTA, the plurality of detection results are acquired by inputting the plurality of endoscopic image data 71 to the second detector 62, and the result obtained by performing averaging or majority decision on these detection results is used as the detection result.

In the image conversion processing as described above, the image adjustment unit 63 performs different pieces of image conversion processing from each other to generate the false negative endoscopic image data 77a, the false negative endoscopic image data 77b, and the false negative endoscopic image data 77c. It should be noted that different pieces of image conversion processing means that pieces of image conversion processing performed by different parameters in the same image conversion processing method are also different pieces of image conversion processing, and pieces of image conversion processing performed by different methods are also different pieces of image conversion processing.

As described above, the image adjustment unit 63 generates the false negative endoscopic image data 77a, the false negative endoscopic image data 77b, and the false negative endoscopic image data 77c which are subjected to different pieces of image conversion processing, and the second detector 62 outputs the detection results using these different false negative endoscopic image data 77. As a result, the re-detection result 79 based on various types of false negative endoscopic image data 77 can be obtained, and the detection accuracy is improved by integrating these re-detection results 79. Therefore, in the second detector 62, the region-of-interest that is not detected by the first detector 61 can be easily re-detected.

In addition, it is preferable that the plurality of endoscopic image data 71 include the endoscopic image data 71 having different imaging times from each other. As the endoscopic image data 71 having different imaging times from each other, the endoscopic image data 71, which is acquired, for example, before or after a time point at which the endoscope system acquires the false negative endoscopic image data 77 from the false negative endoscopic image data 77 is input to the second detector 62 and the detection result is output, or a preset range before and after the time point, can be adopted and used.

Figure 13:
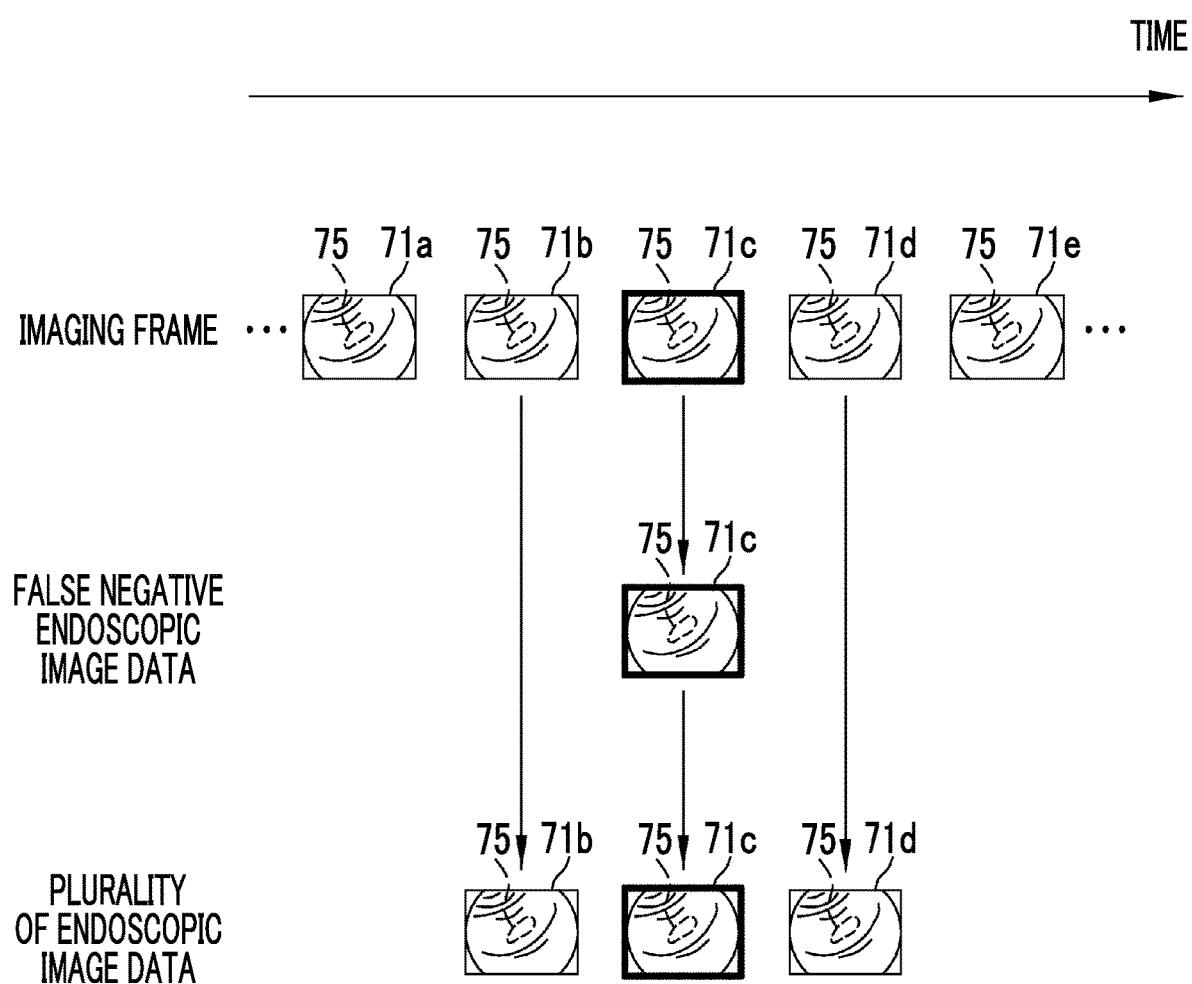
FIG. 13 is an explanatory diagram for describing the endoscopic image data of a plurality of frames.

The endoscope system acquires one endoscopic image data 71 per frame. It should be noted that, in the present specification, the "frame" means a unit of imaging of the examination target by the endoscope system. As shown in FIG. 13, in a period during the examination, the endoscope system 14 acquires endoscopic image data 71a, endoscopic image data 71b, endoscopic image data 71c, endoscopic image data 71d, and endoscopic image data 71e, from the earliest in time series. Out of these endoscopic image data 71, in a case in which the endoscopic image data 71c is the false negative endoscopic image data 77 including the non-detection region-of-interest 75, the second detector 62 uses the endoscopic image data 71b and the endoscopic image data 71d, which are frames before and after the endoscopic image data 71c, as a target of the detection of region-of-interest in the same manner as the endoscopic image data 71c. Thereafter, the detection result into which the plurality of detection results by the endoscopic image data 71b, the endoscopic image data 71c, and the endoscopic image data 71d are integrated is used as the detection result of the region-of-interest of the false negative endoscopic image data 71c. The integration can be performed in the same manner as above.

It should be noted that, in addition to adopting the endoscopic image data 71 immediately before and immediately after the false negative endoscopic image data 77 one frame at a time, a specific plurality of frames immediately before and immediately after a time point at which the false negative endoscopic image data 77 is acquired may be adopted, or the frames separated by a specific number before and after a time point at which the false negative endoscopic image data 77 is acquired may be adopted.

In the second detection unit 55, the plurality of endoscopic image data 71 having different imaging times from each other are input to the second detector 62, and the output plurality of re-detection results 79 are integrated, so that it is possible to detect the region-of-interest that is difficult to be confirmed with one endoscopic image data 71 and is easier to be understood by confirming the endoscopic image data 71 in time series.

As described above, the image adjustment unit 63 generates the false negative endoscopic image data 77a, the false negative endoscopic image data 77b, and the false negative endoscopic image data 77c which are subjected to different pieces of image conversion processing, and the second detector 62 outputs the detection results using these different false negative endoscopic image data 77. As a result, the re-detection result 79 based on various types of false negative endoscopic image data 77 can be obtained, and the detection accuracy is improved by integrating these re-detection results 79. Therefore, in the second detector 62, the region-of-interest that is not detected by the first detector 61 can be easily re-detected.

As described above, the second detector 62 is different from the first detector 61, and it is preferable that a false negative rate of the re-detection result of the second detector 62 be lower than a false negative rate of the first detector 61. The false negative rate means a ratio of the endoscopic image data 71 in which the detection result is false negative in the total re-detection result or the total detection result to the input endoscopic image data 71. The second detector 62 is a detector that can re-detect the region-of-interest for the endoscopic image data 71 in which the region-of-interest is not detected by the first detector 61 and the detection result is false negative. In a case in which the same endoscopic image data 71 as the endoscopic image data 71 in which the false negative result is false negative in the first detector 61 is input to the second detector 62, there is a high possibility that the result will not be false negative. Therefore, in this case, in the second detector 62, the region-of-interest that is not detected by the first detector 61 can be easily re-detected.

Then, training the first detector 61 using the first medical image data set 81 will be further described. In a case in which the first detector 61 is trained using the first medical image data set 81, it is preferable that the false negative rate in the detection result be lower than before training the first detector 61 using the first medical image data set 81. Therefore, in a case of training the first detector 61 using the first medical image data set 81, it is preferable to perform learning as follows.

It is preferable to train the first detector 61 using the first medical image data set 81 and the initial medical image data set. By performing learning using both the first medical image data set 81 and the initial medical image data set, it is possible to improve successfully the detection of the region-of-interest that fails to be detected by learning using the first medical image data set 81 without impairing the detection accuracy of the region-of-interest constructed by training the first detector 61 using the initial medical image data set.

In addition, it is preferable that weighting is performed on each of the first medical image data set 81 and the initial medical image data set, and then the first detector 61 is trained. As a weighting method, for example, a weight of the first medical image data set 81 can be set larger than a weight of the initial medical image data set, and learning is performed. The training data included in the first medical image data set 81 is training data in which the region-of-interest that cannot be detected by the first detector 61 is included as the annotation. Therefore, by increasing the weight of learning based on these training data, it is possible to detect the region-of-interest that cannot be detected in the detection of the region-of-interest in the first detector 61, which can lead to overcoming the weakness.

On the other hand, the weight of the first medical image data set 81 can be set less than the weight of the initial medical image data set for learning. Since the re-detection result 79 by the second detector 62 is used as the annotation, there is a possibility that the training data included in the first medical image data set 81 is not accurate teacher data. Therefore, by reducing the weight of learning based on these training data, it is possible to improve the detection accuracy while preventing the possibility that the detection accuracy is reduced in the detection of the region-of-interest in the first detector 61.

It is preferable that weighting is performed on each first medical image data set 81 included in a plurality of first medical image data sets 81, and then the first detector 61 is trained. The first medical image data set 81 includes the false negative endoscopic image data 77 and the re-detection result 79 by the second detector 62, for example, in a case in which the plurality of second detectors 62 are present, the re-detection result 79 is obtained by integrating the plurality of re-detection results 79. Here, in the plurality of re-detection results 79 before integration, attention is paid to the dispersion of the plurality of re-detection results 79, and in a case in which the dispersion of the plurality of re-detection results 79 is small, the weight is increased for the first medical image data set 81 consisting of the plurality of re-detection results 79. In a case in which the dispersion of the plurality of re-detection results 79 is small, the same re-detection result 79 is obtained in each of the plurality of second detectors 62, and thus there is a high possibility that the re-detection result 79 is the training data having high accuracy. Therefore, it is possible to improve the detection accuracy of the first detector 61 by training the first detector 61 after increasing the weight of the training data having high accuracy.

It is also preferable to perform learning using the first medical image data set 81 as a soft target. By training the first detector 61 using the region-of-interest included in the re-detection result 79 by the second detector 62 as a soft label, it is possible to efficiently train the first detector 61 with a small number of the first medical image data set 81. In a layer structure of the first detector 61, until the middle process, it is also preferable that the first detector 61 be trained by adjusting the parameter such that the parameter is the same as the first detector 61 before learning using the first medical image data set 81.

It should be noted that it is preferable that the false negative endoscopic image data 77 included in the first medical image data set 81 be acquired at a specific facility. It is preferably that the specific facility be a facility that acquires the endoscopic image data 71 used for detecting the region-of-interest by the first detector 61, and it is preferably that the specific facility be the first medical image data set 81 acquired at the facility. As a result, for example, in the first detector 61 included in the diagnosis support system installed at the specific facility, learning specialized for the endoscopic image data 71 acquired at the facility can be performed, and the detection of the region-of-interest for the endoscopic image data 71 acquired at the facility can be performed with higher accuracy, which is preferable.

Then, a timing of the detection by the first detector 61 or the re-detection by the second detector 62 and the like will be further described. With the information processing apparatus 18, it is preferable that the first detector 61 detect the region-of-interest based on the acquired endoscopic image data 71 during the in which the endoscopic image data 71 is acquired. Then, during the same examination, it is preferable to receive information for specifying the endoscopic image data 71 evaluated as false negative by the doctor 76.

The endoscopic image data 71 is obtained by imaging with the endoscope provided in the endoscope system during the endoscopic examination (see FIG. 5). During the endoscopic examination, the endoscopic image data 71 obtained by imaging with the endoscope is displayed on the display 16 as a motion picture. The first detector 61 acquires the obtained endoscopic image data 71 and detects the region-of-interest. The display 16 is controlled by the controller 31 to display at least the endoscopic image data 71, which has the detection result indicating that the region-of-interest is not detected.

Figure 14:
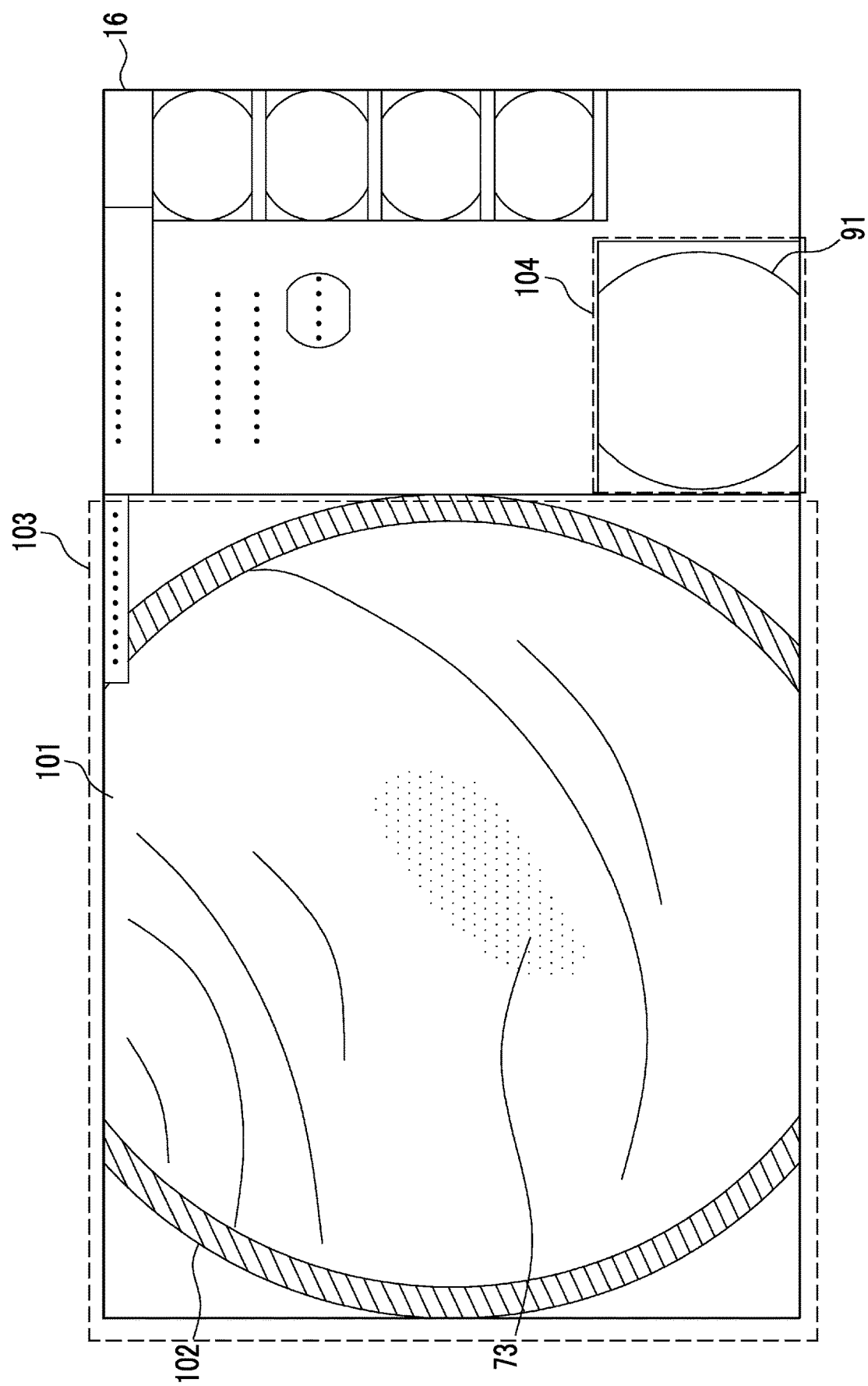
FIG. 14 is an image diagram of a display that displays false negative endoscopic image data.

Regarding the display of the endoscopic image data 71, which has the detection result indicating that the region-of-interest is not detected, the endoscopic image data 71 need only displayed by a method that allows the doctor 76 to recognize that the region-of-interest is not detected in the displayed endoscopic image data 71, as shown in FIG. 14, for example, in a case in which the endoscopic image data 71 is displayed on the display 16 as an endoscopic image 101, as the detection result by the first detector 61, it is shown by a frame 102 of a specific color indicating that the region-of-interest is not detected. In the display 16, the endoscopic image 101 is displayed in an endoscopic image region 103, and the detection result 91 is displayed in a detection result region 104. The detection result 91 may be superimposed on the endoscopic image 101 and displayed in the endoscopic image region 103. The case of FIG. 14 is a case in which the endoscopic image 101 includes the region-of-interest 73, and the detection result 91 or the frame 102 has the detection result indicating that there is not region-of-interest, and thus the false negative endoscopic image data 77 is displayed on the display 16.

In a case in which the doctor 76 looks at the endoscopic image 101 and the detection result 91 displayed on the display 16 and determines that the region-of-interest 73 is present in the examination target, the doctor 76 issues the information for specifying that the endoscopic image data 71 is the false negative endoscopic image data 77. Examples of the method include methods, such as pressing a specific scope button provided in the endoscope, issuing voice using voice recognition, and pressing a foot switch provided in the endoscope system in a case in which the endoscopic image data 71 is displayed on the display 16.

By the method described above, the doctor 76 can issue the information for specifying the endoscopic image data 71 evaluated as false negative during the examination. As a result, it is possible to save time and effort of specifying the endoscopic image data 71 evaluated as false negative after the examination. It should be noted that, during the examination, in a case in which the doctor 76 diagnoses that the examination target includes the region-of-interest, the doctor 76 often presses a freeze button provided in the endoscope to acquire a still picture. Therefore, the freeze button and the scope button for specifying the endoscopic image data 71 evaluated as false negative may be combined. By referring to an acquisition time point of the still picture and the detection result 91 of the first detector 61 at that time point, it is possible to automatically discriminate whether or not the endoscopic image data 71 is evaluated as false negative.

The specification information reception unit 54 (see FIG. 4) receives the information of the endoscopic image data 71 specified by the doctor 76. As described above, since it is possible to easily evaluate that the examination result is false negative during the examination, it is possible to efficiently specify the false negative endoscopic image data 77 without taking a time to evaluate the false negative endoscopic image data 77.

It is preferable that the second detector 62 re-detect the region-of-interest during the examination based on the false negative endoscopic image data 77. The second detector 62 detects the region-of-interest in the background based on the false negative endoscopic image data 77. In a case in which the region-of-interest is detected, by displaying the detection result on the display 16, the doctor 76 can obtain the re-detection result by the second detector 62 for the endoscopic image data 71 evaluated as the false negative endoscopic image data 71 by himself/herself.

In addition, after the in which the endoscopic image data 71 is acquired, the region-of-interest may be detected based on the endoscopic image data 71 acquired by the first detector 61. Then, for example, in a case of creating an examination report, the information for specifying the endoscopic image data 71 evaluated as false negative by the doctor 76 may be received. In a case of creating the examination report, in many cases, the endoscopic image to be inserted in the examination report is selected from among the still pictures acquired by the doctor 76 during the examination. The still picture acquired by the doctor 76 during the examination often reflects the lesion with a high image quality without blurriness or image shake. The false negative endoscopic image data 77, which is such a still picture, in which the region-of-interest cannot be detected in the first detector 61 is the region-of-interest that is difficult to be detected, in which the region-of-interest cannot be detected by the first detection unit 52 even in a case of high image quality, and thus the false negative endoscopic image data 77 is also valuable as the training data. Therefore, evaluating the false negative endoscopic image data 77 by the doctor 76 after the examination is effective for generating the good first medical image data set 81.

In addition, in a case in which the first detector 61 detects the region-of-interest after the examination, it is not necessary to increase a detection speed of the first detector 61 to be close to real time. In addition, since the doctor 76 creates the examination report after the examination, the creation of the examination report and the evaluation of the false negative endoscopic image data 77 can be simultaneously performed, so that the false negative endoscopic image data 77 can be efficiently specified. In addition, since the doctor 76 can obtain the detection result for the endoscopic image data 71 evaluated as the false negative endoscopic image data 71 by himself/herself, these results can be referred to, which can lead to the creation of the examination report with high accuracy.

In addition, the doctor 76 may also evaluate the false negative endoscopic image data 77 both during the examination and after the examination. For example, as described above, the doctor 76 makes a rough record of a case evaluated that there is any possibility of the false negative endoscopic image data 77 during the examination. Then, after the examination, the evaluation as the false negative endoscopic image data 77 is confirmed by referring to the record. The record may be a record of a time point at which the endoscopic image data 71 having a possibility being the false negative endoscopic image data 77 is acquired during the examination, or the record may be tagged with the endoscopic image data 71 itself. As a result, even in a case in which the false negative endoscopic image data 77 cannot be evaluated over time during the examination, the false negative endoscopic image data 77 can be more appropriately evaluated without time and effort of searching for the acquired endoscopic image data 71 after the examination. By evaluating the appropriate false negative endoscopic image data 77, the useful first medical image data set 81 can be generated.

It should be noted that the control of displaying, on the display 16, the endoscopic image data 71 and the detection result of the region-of-interest by the first detector 61 based on the endoscopic image data 71 may be performed. The endoscopic image data 71 and the detection result of the region-of-interest by the first detector 61 may be superimposed on the endoscopic image data 71 and displayed on the display 16, or may be displayed in different regions of the display 16.

Figure 15:
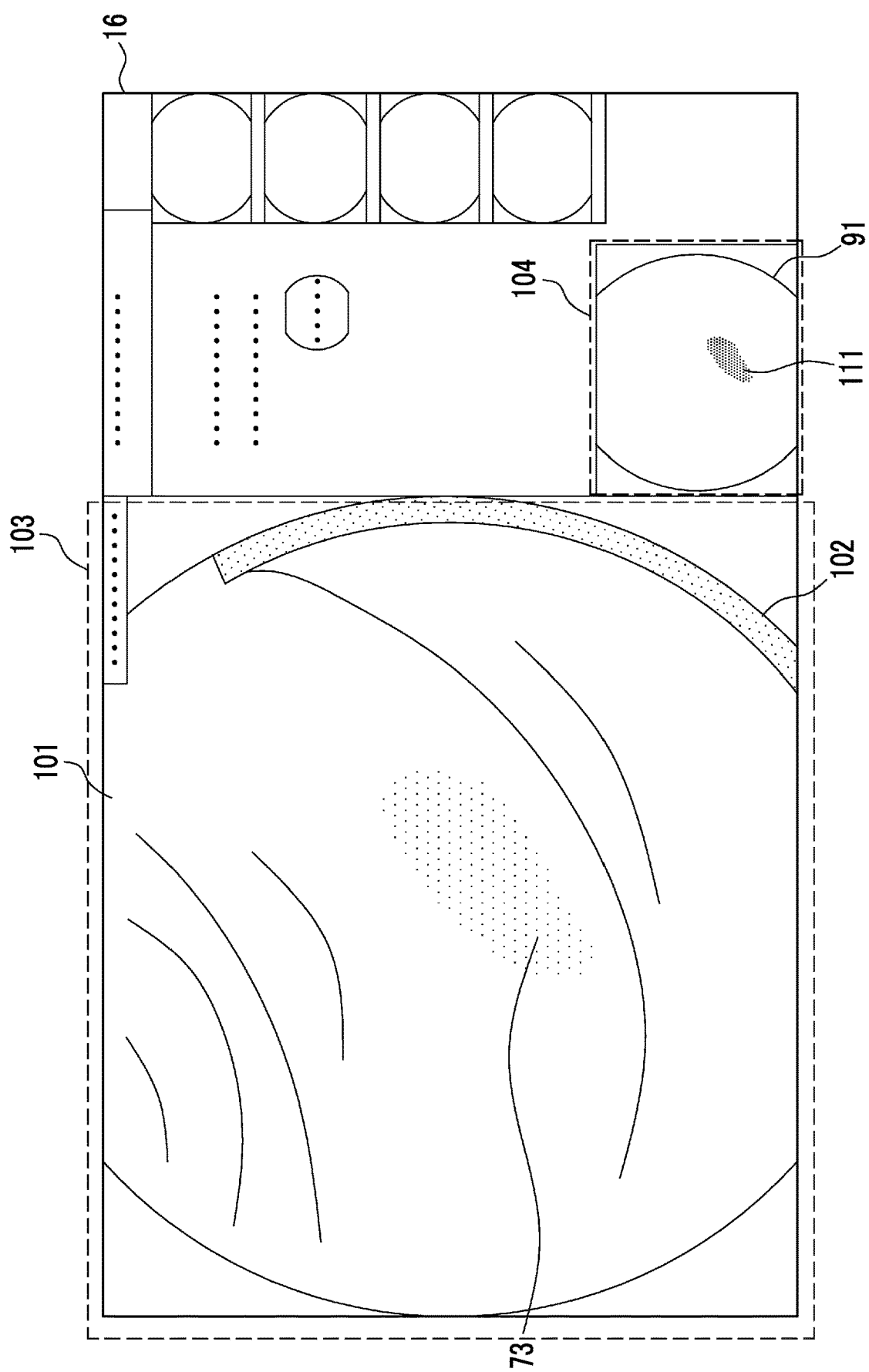
FIG. 15 is an image diagram of the display that displays an appropriate detection result and the endoscopic image data having a region-of-interest.
Figure 16:
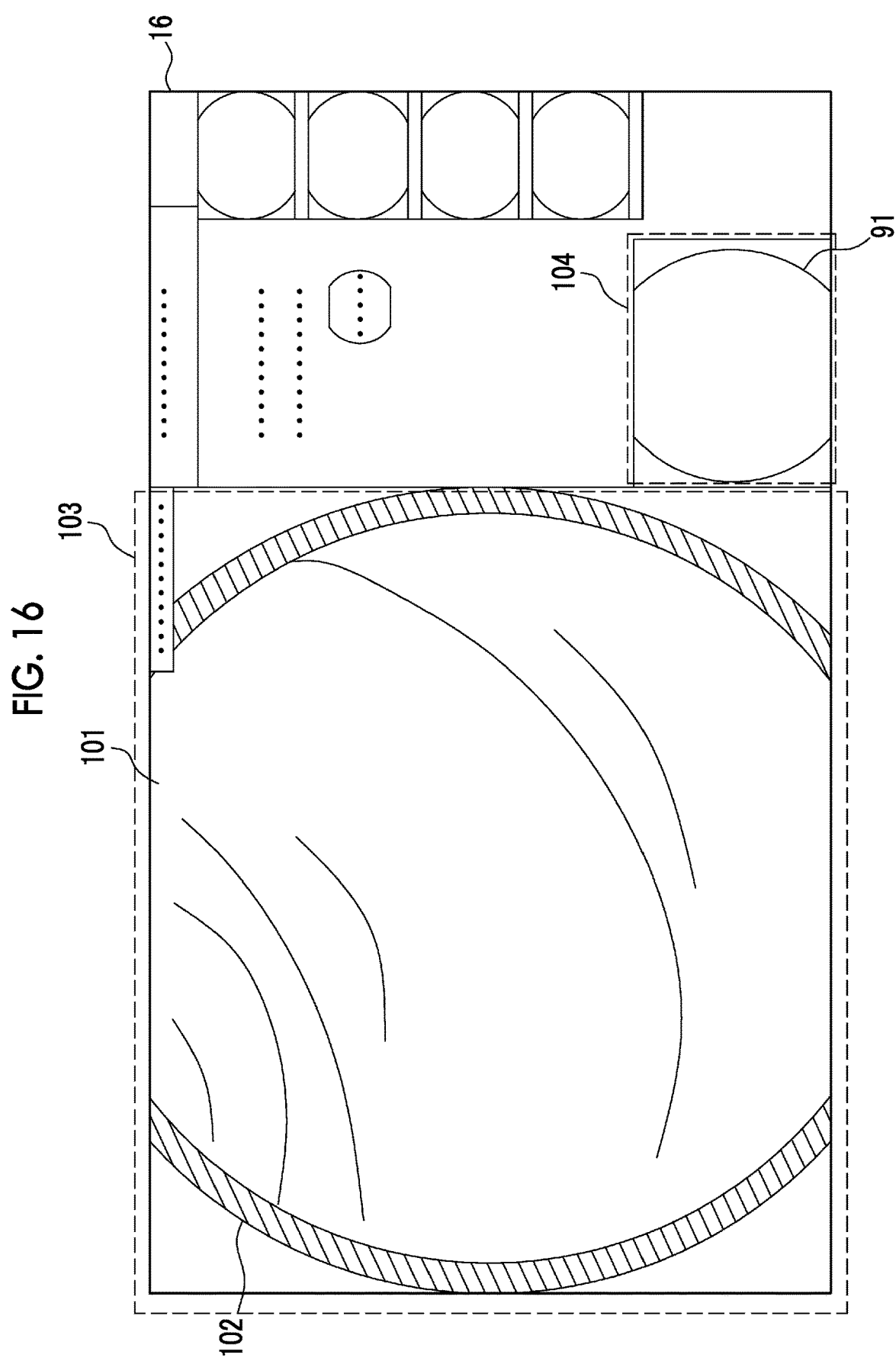
FIG. 16 is an image diagram of the display displaying the appropriate detection result and the endoscopic image data having no region-of-interest.
Figure 17:
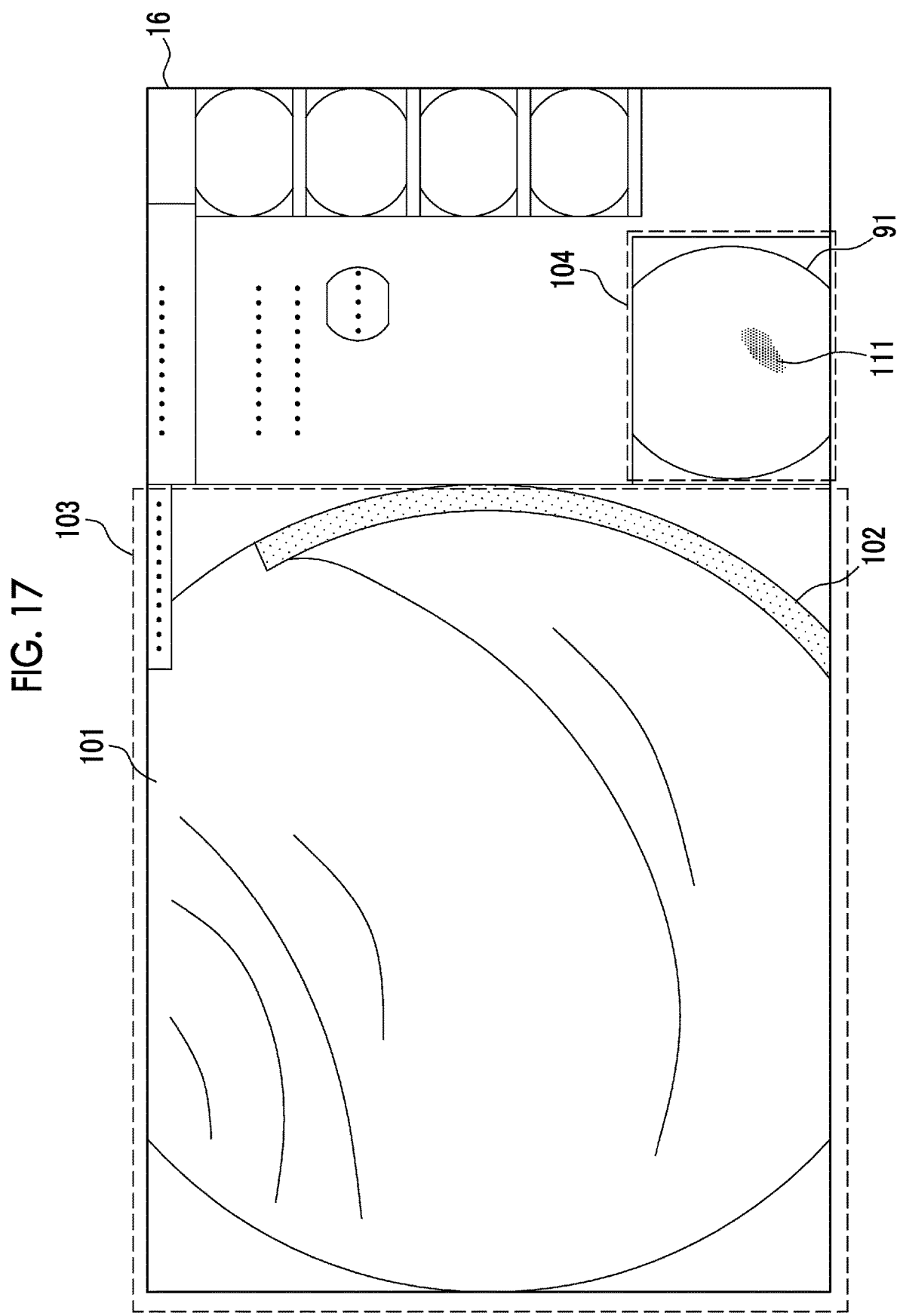
FIG. 17 is an image diagram of the display that displays the false positive endoscopic image data.

As shown in FIG. 15, 16, or 17, the endoscopic image 101 based on the endoscopic image data 71 and the detection result 91 of the region-of-interest by the first detector 61 based on the endoscopic image data 71 can be displayed on the display 16 in different regions, that are, the endoscopic image region 103 and the detection result region 104. The case shown in FIG. 15 is a case in which the endoscopic image data 71 includes the region-of-interest 73, and the detection result 91 of the region-of-interest by the first detector 61 based on the endoscopic image data 71 is displayed by the detection region-of-interest 111 or the frame 102. In this case, the endoscopic image data 71 includes the region-of-interest 73, and the detection region-of-interest 111 is also displayed in the detection result 91 by the first detector 61. Therefore, this case is a case in which the detection result of the first detector 61 is appropriate.

The case shown in FIG. 16 is a case in which the endoscopic image data 71 does not include the region-of-interest 73 and it is displayed that the region-of-interest 73 is not detected in the detection result 91 of the region-of-interest by the first detector 61 based on the endoscopic image data 71, and this case is also a case in which the detection result of the first detector 61 is appropriate.

The case shown in FIG. 17 is a case in which the endoscopic image data 71 does not include the region-of-interest 73 but it is displayed, by the detection region-of-interest 111 or the frame 102, that the region-of-interest 73 is detected in the detection result 91 of the region-of-interest by the first detector 61 based on the endoscopic image data 71, and this case is a case in which the false positive endoscopic image data is displayed on the display 16.

By displaying the detection result of the region-of-interest on the display 16 regardless of the content of the detection result, the doctor 76 can look at the displayed endoscopic image data 71 and the detection result, and can make his/her own diagnosis more appropriate. In addition, in the case of FIG. 17, it can be evaluated that the detection result by the first detector 61 is the false positive detection result. The endoscopic image data 71 evaluated as false positive can be used as the training data for the first detector 61. The endoscopic image data 71 evaluated as false positive can be used as the training data by uniformly adding the annotation indicating that the entire endoscopic image data 71 is a region-of-non-interest. As such an annotation, for example, the annotation, such as the background, for entire false positive endoscopic image data 131 need only be added.

Figure 18:
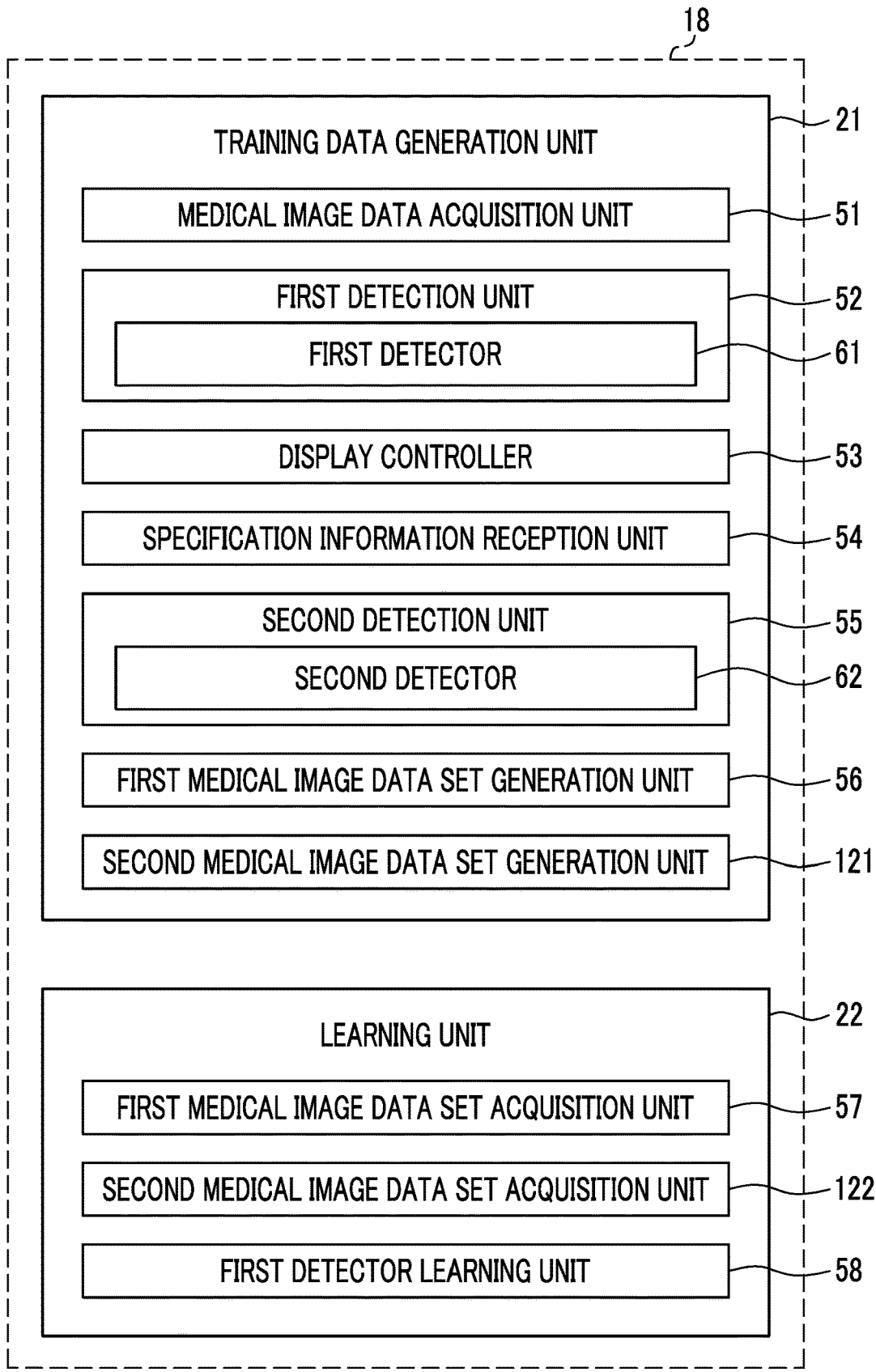
FIG. 18 is a block diagram showing a function of the information processing apparatus comprising a second medical image data set generation unit.

As shown in FIG. 18, in a case in which the false positive detection result is used as the training data, the information processing apparatus 18 comprises a second medical image data set generation unit 121 in the training data generation unit 21, and comprises a second medical image data set acquisition unit 122 in the learning unit 22.

The second medical image data set generation unit 121 generates a second medical image data set including the false positive endoscopic image data 131 which is the endoscopic image data in which the detection result by the first detector 61 is evaluated as the false positive detection result by the doctor 76, and the annotation indicating that the false positive endoscopic image data 131 is the region-of-non-interest.

The specific method can be the same as in the case of false negative, and the specification information reception unit 54 (see FIG. 4) receives the information for specifying the endoscopic image data 71 evaluated that the detection result is false positive by the doctor 76. The second medical image data set generation unit 121 generates the second medical image data set by uniformly adding the annotation, such as "background", to the false positive endoscopic image data 131. The second medical image data set is acquired by the second medical image data set acquisition unit 122 and used for training the first detector 61.

By training the first detector 61 using the second medical image data set including the false positive endoscopic image data, for example, in the first detector 61 adjusted in a way of reducing the false negative detection result, it is possible to reduce the false positive detection result in a case in which the false positive detection result is increased, so that it is possible to improve the detection accuracy of the first detector 61 as a whole.

As described above, with the information processing apparatus 18, in a case in which the region-of-interest is detected using the endoscopic image data 71, it is possible to efficiently improve the detection accuracy.

Figure 19:
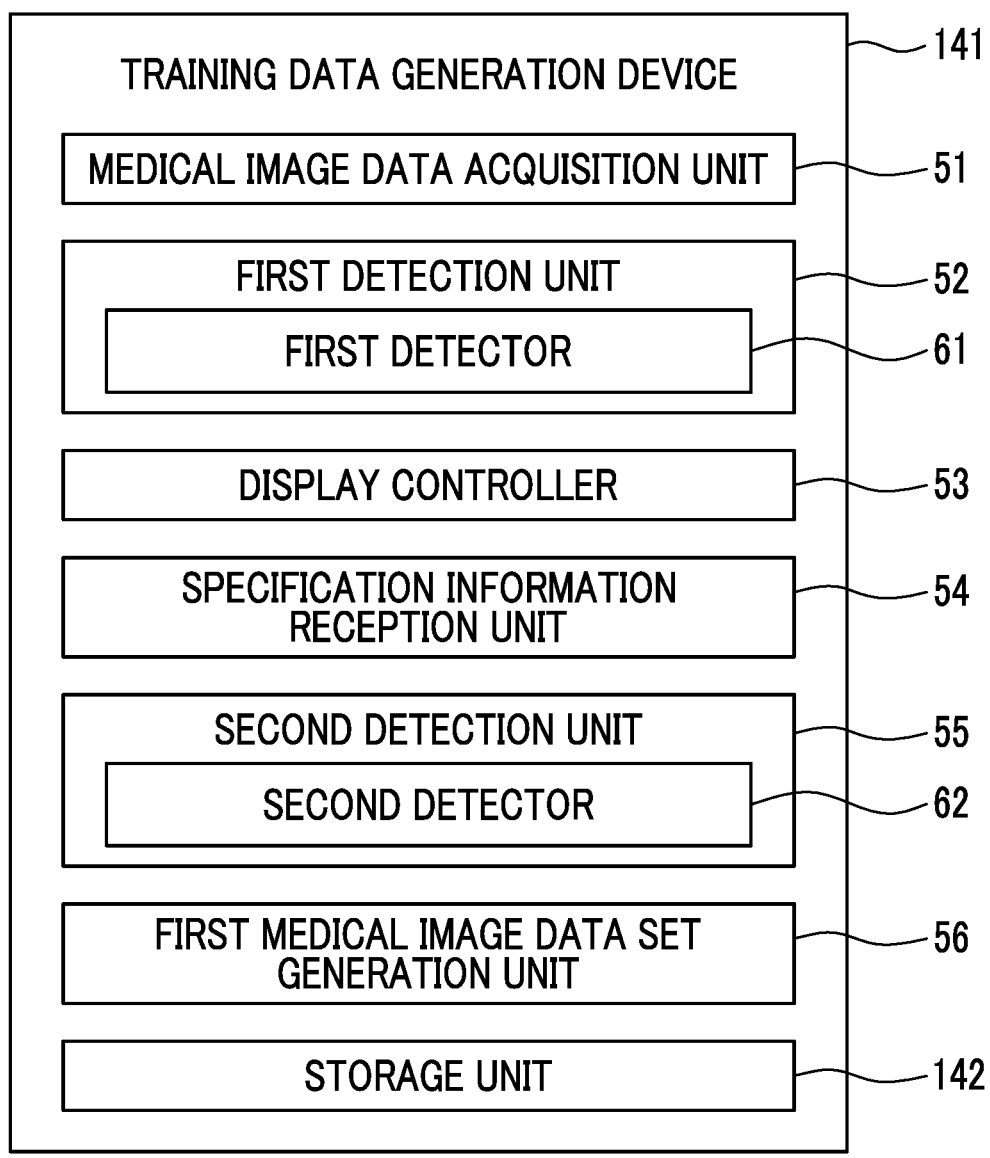
FIG. 19 is a block diagram showing a function of a training data generation device comprising a storage unit.

Then, a training data generation device 141 will be further described. As shown in FIG. 19, the training data generation device 141 is a device in which the training data generation unit 21 is a single device, and the parts having the same reference numerals in the training data generation unit 21 are the same as the parts in description regarding the training data generation unit 21. In the following, the points different from the training data generation unit 21 described above will be described.

The training data generation device 141 comprises a storage unit 142. The storage unit 142 is set in advance in the training data generation device 141, and stores the generated second medical image data set. The stored second medical image data set is used for training the detector as the training data.

The training data generation device 141 can automatically store the training data effective for improving the detection accuracy of the detector. The stored training data can be used in various ways. For example, it can be conveniently used for moving the stored training data or processing the training data itself.

Then, the diagnosis support system 10 will be further described. The diagnosis support system 10 (see FIG. 1) comprises the information processing apparatus 18 and the detection device 13 described above. The parts of the same reference numerals in the information processing apparatus 18 are the same as the parts in the description of the information processing apparatus 18. In the following, the points different from the information processing apparatus 18 described above will be described.

Figure 20:
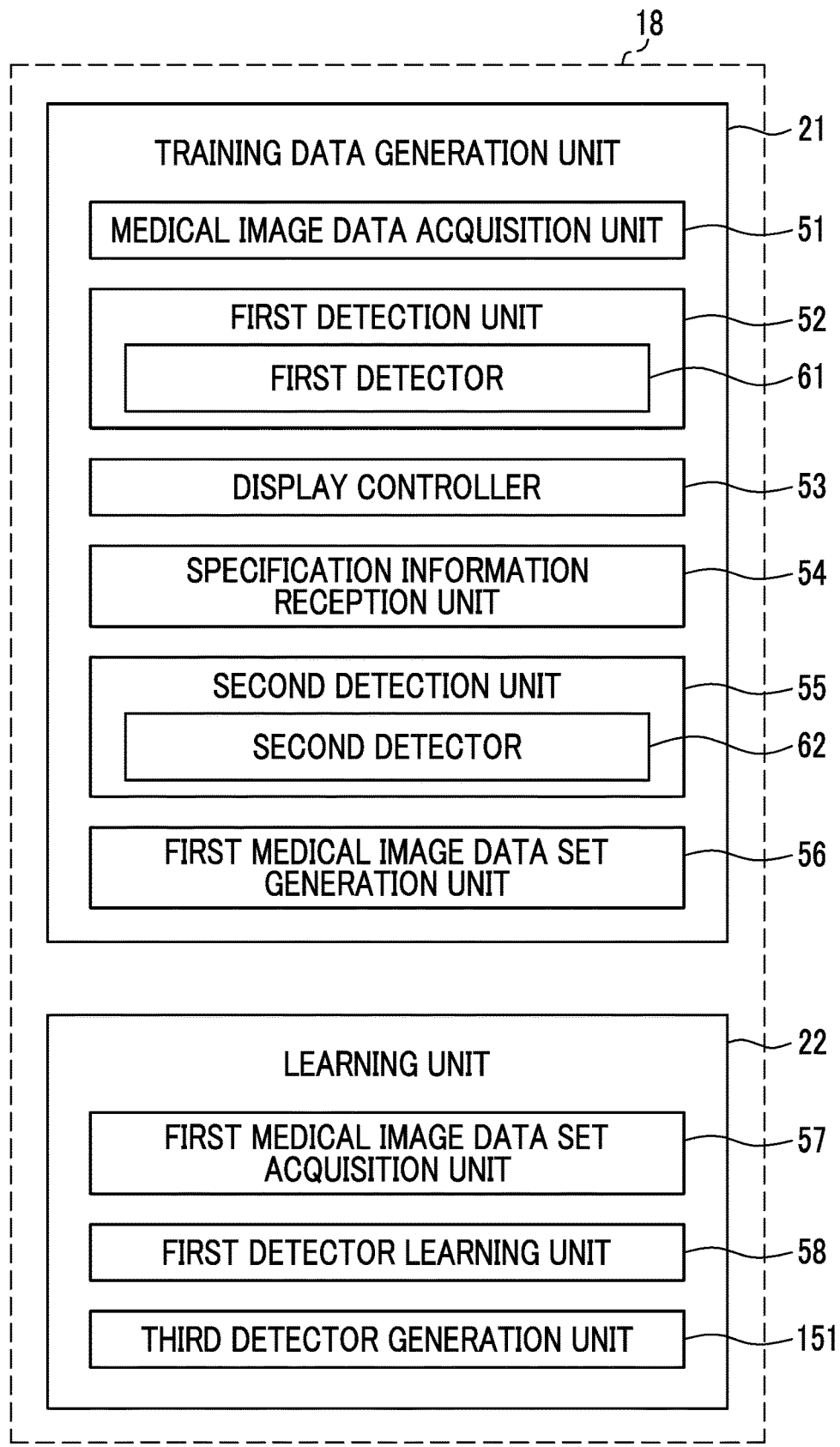
FIG. 20 is a block diagram showing a function of the information processing apparatus comprising a third detector generation unit.

As shown in FIG. 20, the diagnosis support system 10 comprises a third detector generation unit 151 in the learning unit 22 of the information processing apparatus 18. The third detector generation unit 151 acquires the first detector 61 that has been trained by the first detector learning unit 58, and uses the acquired first detector 61 as a third detector 152.

Figure 21:
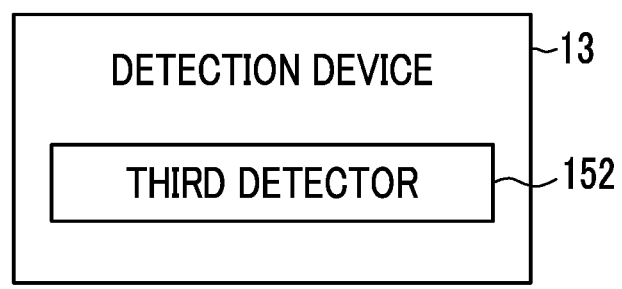
FIG. 21 is a block diagram showing a function of a detection device comprising a third detector.

As shown in FIG. 21, the detection device 13 comprises the third detector 152. The detection device 13 generates the diagnosis support information related to the examination target by detecting the region-of-interest included in the examination target reflected in the endoscopic image data 71 based on the endoscopic image data 71 using the third detector 152. The generated diagnosis support information is controlled to be displayed on the display 16.

The display 16 displays the endoscopic image data 71 acquired by the endoscope system and the diagnosis support information which is the detection result by the third detector 152 based on the endoscopic image data 71 (see FIGS. 14 to 17). The doctor 76 can make a diagnosis of the examination target with reference to the endoscopic image data 71 displayed on the display 16 and the diagnosis support information.

It should be noted that, it is preferable that the third detector generation unit 151 replace the third detector 152 with the first detector 61 after generating the third detector 152. The third detector 152 functions as the first detector 61 after being replaced with the first detector 61. In this case, the first detector 61 is the third detector 152 constructed in the past. That is, the first detector 61 is automatically and continuously updated by the third detector 152. Therefore, since the diagnosis support system 10 comprises the information processing apparatus 18, the third detector 152 automatically and continuously improves the detection accuracy. Therefore, the diagnosis support system 10 is a system that can automatically and continuously detect the region-of-interest based on the endoscopic image data 71 by the third detector 152 having improved detection accuracy.

As described above, with the diagnosis support system 10, the information processing apparatus 18, or the training data generation device 11, the first medical image data set for training the first detector is automatically generated from the false negative medical image data selected by the user. Moreover, by the first detector that first detects the region-of-interest of the medical image data and the second detector that is different from the first detector, the first medical image data set having a more accurate annotation can be generated even in a case in which the inference of the first detector is wrong. In addition, by setting the detection accuracy of the second detector to be higher than that of the first detector, highly accurate inference can be performed and a more accurate first medical image data set can be created. In addition, since the first medical image data set is particularly effective training data for the first detector, the accuracy of the first detector is more reliably improved by re-training the first detector using the first medical image data set. In addition, since the first medical image data set is automatically stored, it is possible to automatically store and accumulate high-quality training data. In addition, since the diagnosis support system 10 automatically improves the detection accuracy for the medical image data, the detection accuracy can be improved without any time and effort even in a case in which the detector is once constructed, and the improvement of the detection accuracy can be automatically and continuously performed.

It should be noted that a plurality of displays 16 may be present, and may include a small portable terminal device, such as a tablet (not shown). In a case of display, a layout of the screen and the like can be set in advance in accordance with the display device.

In the embodiment described above, a hardware structure of a processing unit, such as the controller 31 that executes various pieces of processing in the training data generation unit 21 and the learning unit 22 provided in the information processing apparatus 18, which is the processor device, or the detection device 13 provided in the diagnosis support system 10, is various processors as described below. Examples of the various processors include a central processing unit (CPU), which is a general-purpose processor that executes software (program) to function as various processing units, a programmable logic device (PLD), which is a processor of which a circuit configuration is changeable after manufacturing, such as a field programmable gate array (FPGA), and a dedicated electric circuit, which is a processor having a circuit configuration designed exclusively for executing various pieces of processing.

One processing unit may be composed of one of these various processors, or may be composed of a combination of two or more same type or different type of processors (for example, a plurality of FPGAs, or a combination of a CPU and an FPGA). In addition, a plurality of processing units may be composed of one processor. As an example in which the plurality of processing units are composed of one processor, first, there is a form in which one processor is composed of a combination of one or more CPUs and software, and this processor functions as the plurality of processing units, as represented by a computer, such as a client or a server. Second, as represented by a system on chip (SoC) or the like, there is a form of using a processor that realizes the functions of the entire system including the plurality of processing units with one integrated circuit (IC) chip. As described above, various processing units are composed of one or more of the various processors described above as the hardware structure.

More specifically, the hardware structure of these various processors is an electrical circuit (circuitry) in a form of a combination of circuit elements, such as semiconductor elements.

EXPLANATION OF REFERENCES

10: diagnosis support system
11, 141: training data generation device
12: learning device
13: detection device
14: endoscope system
15: PACS
16: display
17: input device
18: information processing apparatus
21: training data generation unit
22: learning unit
31: controller
32: communication unit
33: storage unit
34: data bus
35: network
41: CPU
42: RAM
43: ROM
44: training data generation unit program
45: training data generation unit data
46: learning unit program
47: learning unit data
51: medical image data acquisition unit
52: first detection unit
53: display controller
54: specification information reception unit
55: second detection unit
56: first medical image data set generation unit
57: first medical image data set acquisition unit
58: first detector learning unit
61: first detector
62: second detector
62a: second detector
62b: second detector
62c: second detector
63: image adjustment unit
71, 71a, 71b, 71c, 71d, 71e: endoscopic image data
72: region-of-interest non-detection endoscopic image data
73: region-of-interest
74: region-of-interest detection endoscopic image data
75: non-detection region-of-interest
76: doctor
77: false negative endoscopic image data
78: adjusted endoscopic image
79, 79a, 79b, 79c: re-detection result
81: first medical image data set
91: detection result
101: endoscopic image
102: frame
103: endoscopic image region
104: detection result region 111: detection region-of-interest
121: second medical image data set generation unit
122: second medical image data set acquisition unit
131: false positive endoscopic image data
142: storage unit
151: third detector generation unit
152: third detector

What is claimed is:

1. An information processing apparatus comprising:
a processor configured to:
  acquire a plurality of medical image data;
  detect, by a first detector, a region-of-interest from the plurality of the medical image data;
  display, on a display, a plurality of first medical image data whose detection result indicates that the region-of-interest is not detected among the plurality of medical image data;
  receive information for specifying a second medical image data evaluated that whose detection result is false negative by a user among the plurality of first image data;
  re-detect, by a second detector, the region-of-interest from the second image data;
  generate a first medical image data set including the second image data and a re- detection result of the region-of-interest of the second medical image data; and
  train the first detector using the first medical image data set;
wherein an operation load of the second detector is higher than an operation load of the first detector.

2. The information processing apparatus according to claim 1,
wherein the second detector is constructed using a machine learning algorithm, and
the number of parameters of the second detector is larger than the number of parameters of the first detector.

3. The information processing apparatus according to claim 1,
wherein the second detector re-detects the region-of-interest based on the medical image data having a higher resolution as compared with the medical image data for the first detector.

4. The information processing apparatus according to claim 1,
wherein the second detector re-detects the region-of-interest based on each of a plurality of the second medical image data, and
the processor is configured to integrate a plurality of the re-detection results based on the plurality of second medical image data, into the re-detection result by the second detector.

5. The information processing apparatus according to claim 4,
wherein a plurality of the second detectors are present, and
each of the second detectors re-detects the region-of-interest based on at least one of the plurality of second medical image data.

6. The information processing apparatus according to claim 4,
wherein the plurality of second medical image data include the second medical image data having different resolutions from each other.

7. The information processing apparatus according to claim 4,
wherein the plurality of second medical image data include the second medical image data subjected to different pieces of image conversion processing from each other.

8. The information processing apparatus according to claim 4,
wherein the plurality of second medical image data include the second medical image data having different imaging times from each other.

9. The information processing apparatus according to claim 1,
wherein a false negative rate of the re-detection result of the second detector is lower than a false negative rate of the detection result of the first detector.

10. The information processing apparatus according to claim 1,
wherein the first detector is constructed in advance by training a machine learning algorithm using an initial medical image data set, and
the processor is configured to train the first detector using the first medical image data set and the initial medical image data set.

11. The information processing apparatus according to claim 10,
wherein the processor is configured to perform weighting on each of the initial medical image data set and the first medical image data set, and then train the first detector.

12. The information processing apparatus according to claim 1,
wherein the processor is configured to perform weighting on each first medical image data set included in a plurality of the first medical image data sets, and then train the first detector.

13. The information processing apparatus according to claim 1,
wherein the medical image data included in the first medical image data set is acquired at a specific facility.

14. The information processing apparatus according to claim 1,
wherein the processor is configured to:
  detect, by the first detector, the region-of-interest based on the medical image data during examination in which the medical image data is acquired; and
  receive information for specifying the second medical image data.

15. The information processing apparatus according to claim 14,
wherein the processor is configured to re-detect, by the second detector, the region-of- interest based on the second medical image data during the examination.

16. The information processing apparatus according to claim 1,
wherein the processor is configured to, on the display, the medical image data and the detection result of the region-of-interest based on the medical image data.

17. The information processing apparatus according to claim 16,
wherein the processor is configured to:
  receive information for specifying the second medical image data;
  generate a second medical image data set including the second medical image data and an annotation indicating that the second medical image data is of a region-of-non-interest; and
  train the first detector using the second medical image data set.

18. A training data generation device comprising:
a processor configured to:
- acquire a plurality of medical image data;
- detect, by a first detector, a region-of-interest from the plurality of the medical image data;
- display, on a display, a plurality of first medical image data whose detection result indicates that the region-of-interest is not detected among the plurality of medical image data;
- receive information for specifying a second medical image data evaluated that whose detection result is false negative by a user among the plurality of first image data;
- re-detect, by a second detector, the region-of-interest from the second image data;
- generate a medical image data set including the second medical image data and a re- detection result of the region-of-interest associated with the second medical image data; and
- store the medical image data set in a storage in advance;

wherein an operation load of the second detector is higher than an operation load of the first detector.

19. A diagnosis support system comprising:
a processor configured to:
- acquire a plurality of medical image data;
- detect, by a first detector, a region-of-interest from the plurality of the medical image data;
- display, on a display, a plurality of first medical image data whose detection result indicates that the region-of-interest is not detected among the plurality of medical image data;
- receive information for specifying a second medical image data evaluated that whose detection result is false negative by a user among the plurality of first image data;
- re-detect, by a second detector, the region-of-interest from the second image data;
- generate a medical image data set including the second medical image data and a re- detection result of the region-of-interest associated with the second medical image data;
- generate a third detector by training the first detector using the medical image data set; and
- generate diagnosis support information related to the examination target by detecting, by the third detector, the region-of-interest included in the examination target reflected in the medical image data based on the medical image data;

wherein an operation load of the second detector is higher than an operation load of the first detector.

20. The diagnosis support system according to claim 19, wherein the first detector is the third detector constructed in the past.

* * * * *